(12) United States Patent
Anderson

(10) Patent No.: US 10,823,721 B2
(45) Date of Patent: Nov. 3, 2020

(54) OPTICALLY BASED NANOPORE SEQUENCING

(71) Applicant: QUANTAPORE, INC., Menlo Park, CA (US)

(72) Inventor: Brett N. Anderson, Menlo Park, CA (US)

(73) Assignee: Quantapore, Inc., South San Francisco, CA (US)

( * ) Notice: Subject to any disclaimer, the term of this patent is extended or adjusted under 35 U.S.C. 154(b) by 160 days.

(21) Appl. No.: 16/309,097

(22) PCT Filed: Jun. 22, 2017

(86) PCT No.: PCT/US2017/038813
§ 371 (c)(1),
(2) Date: Dec. 11, 2018

(87) PCT Pub. No.: WO2018/009346
PCT Pub. Date: Jan. 11, 2018

(65) Prior Publication Data
US 2019/0120817 A1    Apr. 25, 2019

Related U.S. Application Data

(60) Provisional application No. 62/358,552, filed on Jul. 5, 2016.

(51) Int. Cl.
*G01N 33/487* (2006.01)
*G01N 27/447* (2006.01)
(Continued)

(52) U.S. Cl.
CPC ..... *G01N 33/48721* (2013.01); *C12Q 1/6869* (2013.01); *G01N 27/447* (2013.01);
(Continued)

(58) Field of Classification Search
None
See application file for complete search history.

(56) References Cited

U.S. PATENT DOCUMENTS

| 4,161,690 A | 7/1979 | Feier |
| 4,962,037 A | 10/1990 | Jett et al. |

(Continued)

FOREIGN PATENT DOCUMENTS

| CN | 1403817 | 3/2003 |
| CN | 201302544 | 9/2009 |

(Continued)

OTHER PUBLICATIONS

US 8,008,014 B2, 08/2011, Gershow et al. (withdrawn)
(Continued)

*Primary Examiner* — Robert T. Crow
(74) *Attorney, Agent, or Firm* — Stephen C. Macevicz; Vincent M. Powers; Levine Bagade Han LLP

(57) ABSTRACT

In some aspects the invention is directed to methods of analyzing a polynucleotide which include steps of directing to a nanopore an excitation beam having a predetermined polarization state; translocating a polynucleotide through the nanopore, wherein nucleotides of the polynucleotide are labeled with fluorescent labels having absorption dipoles and wherein the nanopore spatially orients the fluorescent labels so that during translocation the adsorption dipoles are substantially unresponsive to the excitation beam; detecting changes in fluorescent signals generated by the fluorescent labels as nucleotides with fluorescent labels exit the nanopore and absorption dipoles thereof become responsive to excitation by the excitation beam with the predetermined polarization state; and identifying nucleotides exiting the nanopore from the changes in fluorescent signals.

19 Claims, 13 Drawing Sheets

Specification includes a Sequence Listing.

(51) Int. Cl.
*C12Q 1/6869* (2018.01)
*B82Y 5/00* (2011.01)
*B82Y 15/00* (2011.01)
*B82Y 30/00* (2011.01)

(52) U.S. Cl.
CPC ............... *B82Y 5/00* (2013.01); *B82Y 15/00* (2013.01); *B82Y 30/00* (2013.01)

(56) References Cited

U.S. PATENT DOCUMENTS

| | | | |
|---|---|---|---|
| 5,131,755 A | 7/1992 | Chadwick et al. | |
| 5,356,776 A | 10/1994 | Kambara et al. | |
| 5,387,926 A | 2/1995 | Bellan | |
| 5,405,747 A | 4/1995 | Jett et al. | |
| 5,470,705 A | 11/1995 | Grossman et al. | |
| 5,580,732 A | 12/1996 | Grossman et al. | |
| 5,624,800 A | 4/1997 | Grossman et al. | |
| 5,795,782 A | 8/1998 | Church et al. | |
| 5,798,042 A | 8/1998 | Chu et al. | |
| 5,821,058 A | 10/1998 | Smith et al. | |
| 5,945,312 A | 8/1999 | Goodman et al. | |
| 5,989,871 A | 11/1999 | Grossman et al. | |
| 6,015,714 A | 1/2000 | Baldarelli et al. | |
| 6,136,543 A | 10/2000 | Anazawa et al. | |
| 6,210,896 B1 | 4/2001 | Chan | |
| 6,211,955 B1 | 4/2001 | Basiji et al. | |
| 6,249,341 B1 | 6/2001 | Basiji et al. | |
| 6,251,303 B1 | 6/2001 | Bawendi et al. | |
| 6,252,303 B1 | 6/2001 | Huang | |
| 6,263,286 B1 | 7/2001 | Gilmanshin et al. | |
| 6,267,872 B1 | 7/2001 | Akeson et al. | |
| 6,325,968 B1 | 12/2001 | Fricker et al. | |
| 6,335,420 B1 | 1/2002 | Bruening et al. | |
| 6,335,440 B1 | 1/2002 | Lee et al. | |
| 6,355,420 B1 | 3/2002 | Chan | |
| 6,362,002 B1 | 3/2002 | Denison et al. | |
| 6,413,792 B1 | 7/2002 | Sauer et al. | |
| 6,426,231 B1 | 7/2002 | Bayley et al. | |
| 6,428,959 B1 | 8/2002 | Deamer | |
| 6,429,897 B2 | 8/2002 | Derndinger et al. | |
| 6,447,724 B1 | 9/2002 | Jensen et al. | |
| 6,464,842 B1 | 10/2002 | Golovchenko et al. | |
| 6,465,193 B2 | 10/2002 | Akeson et al. | |
| 6,473,176 B2 | 10/2002 | Basiji et al. | |
| 6,498,010 B1 | 12/2002 | Fitzgerald et al. | |
| 6,503,757 B1 | 1/2003 | Chow | |
| 6,504,943 B1 | 1/2003 | Sweatt et al. | |
| 6,511,802 B1 | 1/2003 | Albrecht et al. | |
| 6,528,258 B1 | 3/2003 | Russell | |
| 6,537,755 B1 | 3/2003 | Drmanac | |
| 6,583,865 B2 | 6/2003 | Basiji et al. | |
| 6,608,680 B2 | 8/2003 | Basiji et al. | |
| 6,608,682 B2 | 8/2003 | Ortyn et al. | |
| 6,616,895 B2 | 9/2003 | Dugas et al. | |
| 6,617,113 B2 | 9/2003 | Deamer | |
| 6,618,140 B2 | 9/2003 | Frost et al. | |
| 6,618,679 B2 | 9/2003 | Loehrlein et al. | |
| 6,627,067 B1 | 9/2003 | Branton et al. | |
| 6,671,044 B2 | 12/2003 | Ortyn et al. | |
| 6,673,615 B2 | 1/2004 | Denison et al. | |
| 6,706,203 B2 | 3/2004 | Barth et al. | |
| 6,723,515 B2 | 4/2004 | Barron | |
| 6,743,905 B2 | 6/2004 | Woo et al. | |
| 6,746,594 B2 | 6/2004 | Akeson et al. | |
| 6,752,914 B1 | 6/2004 | Hassard | |
| 6,756,204 B2 | 6/2004 | Grossman et al. | |
| 6,758,961 B1 | 7/2004 | Vogel et al. | |
| 6,772,070 B2 | 8/2004 | Gilmanshin et al. | |
| 6,790,671 B1 | 9/2004 | Austin et al. | |
| 6,821,726 B1 | 11/2004 | Dahm et al. | |
| 6,824,659 B2 | 11/2004 | Bayley et al. | |
| 6,830,670 B1 | 12/2004 | Viovy et al. | |
| 6,855,551 B2 | 2/2005 | Bawendi et al. | |
| 6,856,390 B2 | 2/2005 | Nordman et al. | |
| 6,906,749 B1 | 6/2005 | Fox | |
| 6,916,665 B2 | 7/2005 | Bayley et al. | |
| 6,936,433 B2 | 8/2005 | Akeson et al. | |
| 6,947,128 B2 | 9/2005 | Basiji et al. | |
| 6,952,651 B2 | 10/2005 | Su | |
| 6,975,400 B2 | 12/2005 | Ortyn et al. | |
| 6,982,146 B1 | 1/2006 | Schneider et al. | |
| 6,998,251 B2 | 2/2006 | Guttman et al. | |
| 7,001,792 B2 | 2/2006 | Sauer et al. | |
| 7,005,264 B2 | 2/2006 | Su et al. | |
| 7,008,547 B2 | 3/2006 | Chen et al. | |
| 7,049,104 B2 | 5/2006 | Kambara et al. | |
| 7,052,847 B2 | 5/2006 | Korlach et al. | |
| 7,056,661 B2 | 6/2006 | Korlach et al. | |
| 7,056,676 B2 | 6/2006 | Korlach et al. | |
| 7,060,507 B2 | 6/2006 | Akeson et al. | |
| 7,074,569 B2 | 7/2006 | Woo et al. | |
| 7,129,050 B2 | 10/2006 | Grossman et al. | |
| 7,189,503 B2 | 3/2007 | Akeson et al. | |
| 7,201,836 B2 | 4/2007 | Vogel et al. | |
| 7,235,184 B2 | 6/2007 | Dugas et al. | |
| 7,235,361 B2 | 6/2007 | Bawendi et al. | |
| 7,238,485 B2 | 7/2007 | Akeson et al. | |
| 7,244,349 B2 | 7/2007 | Vogel et al. | |
| 7,248,771 B2 | 7/2007 | Schmidt et al. | |
| 7,250,115 B2 | 7/2007 | Barth | |
| 7,271,896 B2 | 9/2007 | Chan et al. | |
| 7,279,337 B2 | 10/2007 | Zhu | |
| 7,280,207 B2 | 10/2007 | Oldham et al. | |
| 7,285,010 B2 | 10/2007 | Hatakeyama et al. | |
| 7,364,851 B2 | 4/2008 | Berlin et al. | |
| 7,371,533 B2 | 5/2008 | Slater et al. | |
| 7,381,315 B2 | 6/2008 | Grossman et al. | |
| 7,387,715 B2 | 6/2008 | Vogel et al. | |
| 7,390,457 B2 | 6/2008 | Schembri | |
| 7,397,232 B2 | 7/2008 | Hu et al. | |
| 7,410,564 B2 | 8/2008 | Flory | |
| 7,428,047 B2 | 9/2008 | Oldham et al. | |
| 7,438,193 B2 | 10/2008 | Yang et al. | |
| 7,444,053 B2 | 10/2008 | Schmidt et al. | |
| 7,468,271 B2 | 12/2008 | Golovchenko et al. | |
| 7,476,503 B2 | 1/2009 | Turner et al. | |
| 7,553,730 B2 | 6/2009 | Barth et al. | |
| 7,567,695 B2 | 7/2009 | Frost et al. | |
| 7,595,023 B2 | 9/2009 | Lewis et al. | |
| 7,609,309 B2 | 10/2009 | Brown et al. | |
| 7,622,934 B2 | 11/2009 | Hibbs et al. | |
| 7,625,706 B2 | 12/2009 | Akeson et al. | |
| 7,651,599 B2 | 1/2010 | Blaga et al. | |
| 7,666,593 B2 | 2/2010 | Lapidus | |
| 7,670,770 B2 | 3/2010 | Chou et al. | |
| 7,678,562 B2 | 3/2010 | Ling | |
| 7,744,816 B2 | 6/2010 | Su et al. | |
| 7,777,505 B2 | 8/2010 | White et al. | |
| 7,803,607 B2 | 9/2010 | Branton et al. | |
| 7,835,870 B2 | 11/2010 | Nair et al. | |
| 7,838,873 B2 | 11/2010 | Clevenger et al. | |
| 7,843,562 B2 | 11/2010 | Chan et al. | |
| 7,846,738 B2 | 12/2010 | Golovchenko et al. | |
| 7,849,581 B2 | 12/2010 | White et al. | |
| 7,871,777 B2 | 1/2011 | Schneider et al. | |
| 7,883,869 B2 | 2/2011 | Ju et al. | |
| 7,897,338 B2 | 3/2011 | Woo et al. | |
| 7,947,454 B2 | 5/2011 | Akeson et al. | |
| 7,972,858 B2 | 7/2011 | Meller et al. | |
| 8,105,846 B2 | 1/2012 | Bayley et al. | |
| 8,206,568 B2 | 6/2012 | Branton et al. | |
| 8,394,584 B2 | 3/2013 | Timp et al. | |
| 8,394,640 B2 | 3/2013 | Golovchenko et al. | |
| 8,435,775 B2 | 5/2013 | Holliger et al. | |
| 8,440,403 B2 | 5/2013 | Frayling | |
| 8,771,491 B2 | 7/2014 | Huber | |
| 8,802,838 B2 | 8/2014 | Meller et al. | |
| 8,865,078 B2 | 10/2014 | Chiou et al. | |
| 8,865,455 B2 | 10/2014 | Frayling | |
| 9,121,843 B2 | 9/2015 | Meller et al. | |
| 9,862,997 B2 | 1/2018 | Huber et al. | |
| 2002/0034762 A1 | 3/2002 | Muller et al. | |
| 2002/0119455 A1 | 8/2002 | Chan | |

(56) References Cited

U.S. PATENT DOCUMENTS

| | | |
|---|---|---|
| 2003/0003463 A1 | 1/2003 | Rothberg et al. |
| 2003/0064366 A1 | 4/2003 | Hardin et al. |
| 2003/0092005 A1 | 5/2003 | Levene et al. |
| 2003/0096220 A1 | 5/2003 | Lafferty et al. |
| 2003/0143614 A1 | 7/2003 | Drmanac |
| 2003/0148544 A1 | 8/2003 | Nie et al. |
| 2003/0174992 A1 | 9/2003 | Levene et al. |
| 2003/0207326 A1 | 11/2003 | Su et al. |
| 2003/0215881 A1 | 11/2003 | Bayley et al. |
| 2004/0002089 A1 | 1/2004 | Dubertret et al. |
| 2004/0033492 A1 | 2/2004 | Chen |
| 2004/0137158 A1 | 7/2004 | Kools et al. |
| 2004/0146430 A1 | 7/2004 | Dugas |
| 2004/0175710 A1 | 9/2004 | Haushalter |
| 2004/0214221 A1 | 10/2004 | Muehlegger et al. |
| 2005/0014154 A1 | 1/2005 | Weizenegger |
| 2005/0019784 A1 | 1/2005 | Su et al. |
| 2005/0095599 A1 | 5/2005 | Pittaro et al. |
| 2005/0130159 A1 | 6/2005 | Rigler et al. |
| 2005/0136408 A1 | 6/2005 | Tom et al. |
| 2005/0147992 A1 | 7/2005 | Quake et al. |
| 2005/0153284 A1 | 7/2005 | Foldes et al. |
| 2005/0164211 A1 | 7/2005 | Hannah |
| 2005/0186576 A1 | 8/2005 | Chan et al. |
| 2005/0186629 A1 | 8/2005 | Barth |
| 2005/0196876 A1 | 9/2005 | Chan et al. |
| 2005/0227239 A1 | 10/2005 | Joyce |
| 2005/0241933 A1 | 11/2005 | Branton et al. |
| 2005/0282229 A1 | 12/2005 | Su et al. |
| 2006/0003458 A1 | 1/2006 | Golovchenko et al. |
| 2006/0019247 A1 | 1/2006 | Su et al. |
| 2006/0019259 A1 | 1/2006 | Joyce |
| 2006/0063171 A1 | 3/2006 | Akeson et al. |
| 2006/0147942 A1 | 7/2006 | Buzby |
| 2006/0210995 A1 | 9/2006 | Joyce |
| 2006/0231419 A1 | 10/2006 | Barth et al. |
| 2006/0251371 A1 | 11/2006 | Schmidt et al. |
| 2006/0292041 A1 | 12/2006 | Dugas et al. |
| 2007/0012865 A1 | 1/2007 | Katzir et al. |
| 2007/0037199 A1 | 2/2007 | Takahashi et al. |
| 2007/0042366 A1 | 2/2007 | Ling |
| 2007/0054276 A1 | 3/2007 | Sampson |
| 2007/0172858 A1 | 7/2007 | Hardin et al. |
| 2007/0172865 A1 | 7/2007 | Hardin et al. |
| 2007/0190542 A1 | 8/2007 | Ling et al. |
| 2007/0190543 A1 | 8/2007 | Livak |
| 2007/0202008 A1 | 8/2007 | Schembri et al. |
| 2007/0215472 A1 | 9/2007 | Slater et al. |
| 2007/0218494 A1 | 9/2007 | Slater et al. |
| 2007/0224613 A1 | 9/2007 | Strathmann |
| 2007/0231795 A1 | 10/2007 | Su |
| 2007/0264623 A1 | 11/2007 | Wang et al. |
| 2008/0025875 A1 | 1/2008 | Martin et al. |
| 2008/0032290 A1 | 2/2008 | Young |
| 2008/0050752 A1 | 2/2008 | Sun et al. |
| 2008/0187915 A1 | 8/2008 | Polonsky et al. |
| 2008/0193956 A1 | 8/2008 | Kricka et al. |
| 2008/0218184 A1 | 9/2008 | White et al. |
| 2008/0254995 A1 | 10/2008 | Kim et al. |
| 2008/0261204 A1 | 10/2008 | Lexow |
| 2008/0274905 A1 | 11/2008 | Greene |
| 2008/0311375 A1 | 12/2008 | Harnack et al. |
| 2009/0021735 A1 | 1/2009 | Oldham et al. |
| 2009/0024331 A1 | 1/2009 | Tomaney et al. |
| 2009/0029477 A1 | 1/2009 | Meller et al. |
| 2009/0035777 A1 | 2/2009 | Kokoris et al. |
| 2009/0061447 A1 | 3/2009 | Schneider |
| 2009/0066315 A1 | 3/2009 | Hu et al. |
| 2009/0136958 A1 | 5/2009 | Gershow et al. |
| 2009/0137007 A1 | 5/2009 | Korlach et al. |
| 2009/0148348 A1 | 6/2009 | Pettigrew et al. |
| 2009/0185955 A1 | 7/2009 | Nellissen |
| 2009/0222216 A1 | 9/2009 | Hibbs et al. |
| 2009/0250615 A1 | 10/2009 | Oldham et al. |
| 2009/0277869 A1 | 11/2009 | Dugas |
| 2009/0298075 A1 | 12/2009 | Travers et al. |
| 2009/0305278 A1 | 12/2009 | Hardin et al. |
| 2009/0314939 A1 | 12/2009 | Stern et al. |
| 2010/0025249 A1 | 2/2010 | Polonsky et al. |
| 2010/0029508 A1 | 2/2010 | Austin et al. |
| 2010/0035260 A1 | 2/2010 | Olasagasti et al. |
| 2010/0035268 A1 | 2/2010 | Beechem et al. |
| 2010/0075309 A1 | 3/2010 | Maxham et al. |
| 2010/0103416 A1 | 4/2010 | Oldham et al. |
| 2010/0227913 A1 | 9/2010 | Lyakhov et al. |
| 2010/0262379 A1 | 10/2010 | Frazier |
| 2010/0292101 A1 | 11/2010 | So |
| 2010/0331194 A1 | 12/2010 | Turner et al. |
| 2011/0053284 A1 | 3/2011 | Meller et al. |
| 2011/0172404 A1 | 7/2011 | Luo et al. |
| 2011/0177498 A1 | 7/2011 | Clarke et al. |
| 2011/0177978 A1 | 7/2011 | Luo et al. |
| 2011/0257043 A1 | 10/2011 | Meller et al. |
| 2011/0308950 A1 | 12/2011 | Sakai et al. |
| 2012/0055792 A1 | 3/2012 | Gundlach et al. |
| 2012/0135410 A1 | 5/2012 | Soni et al. |
| 2012/0199482 A1 | 8/2012 | Meller et al. |
| 2012/0261261 A1 | 10/2012 | Huber |
| 2013/0040827 A1 | 2/2013 | Macevicz |
| 2013/0176563 A1 | 7/2013 | Ozawa et al. |
| 2013/0203050 A1 | 8/2013 | Huber et al. |
| 2013/0203610 A1 | 8/2013 | Meller et al. |
| 2013/0256118 A1 | 10/2013 | Meller et al. |
| 2014/0087474 A1 | 3/2014 | Huber |
| 2014/0255935 A1 | 9/2014 | Huber |
| 2014/0335513 A9 | 11/2014 | Huber et al. |
| 2014/0367259 A1 | 12/2014 | Frayling et al. |
| 2015/0057948 A1 | 2/2015 | Reid et al. |
| 2015/0204840 A1 | 7/2015 | Soares et al. |
| 2015/0344944 A1 | 12/2015 | Reid et al. |
| 2015/0347675 A1 | 12/2015 | Schuller et al. |
| 2016/0115531 A1 | 4/2016 | Huber et al. |
| 2016/0122812 A1 | 5/2016 | Huber |
| 2016/0162634 A1 | 6/2016 | Reid et al. |
| 2017/0219557 A1 | 8/2017 | Reid et al. |

FOREIGN PATENT DOCUMENTS

| | | |
|---|---|---|
| EP | 1682673 | 7/2006 |
| EP | 2758545 | 6/2017 |
| WO | WO 2001/018247 | 3/2001 |
| WO | WO 2005/045392 | 5/2005 |
| WO | WO 2006/052882 | 5/2006 |
| WO | WO 2007/120265 | 10/2007 |
| WO | WO 2008/049795 | 5/2008 |
| WO | WO 2008/092760 | 8/2008 |
| WO | WO 2009/007743 | 1/2009 |
| WO | WO 2009/020682 | 2/2009 |
| WO | WO 2009/056831 | 5/2009 |
| WO | WO 2009/092035 | 7/2009 |
| WO | WO 2010/002883 | 1/2010 |
| WO | WO 2010/007537 | 1/2010 |
| WO | WO 2010/116595 | 10/2010 |
| WO | WO 2011/040996 | 4/2011 |
| WO | WO 2011/050147 | 4/2011 |
| WO | WO 2011/067559 | 6/2011 |
| WO | WO 2012/121756 | 9/2012 |
| WO | WO 2012/170499 | 12/2012 |
| WO | WO 2013/041878 | 3/2013 |
| WO | WO 2014/066902 | 5/2014 |
| WO | WO 2014/066905 | 5/2014 |
| WO | WO 2014/190322 | 11/2014 |
| WO | WO 2016/065339 | 4/2016 |
| WO | WO 2018/009346 | 1/2018 |

OTHER PUBLICATIONS

Michalet et al, Ann. Rev Biophys. Biomol. Struct, vol. 32, pp. 161-182, published online Feb. 11, 2003.*

Aksimentiev, A. et al., "Microscopic Kinetics of DNA Translocation through Synthetic Nanopores," *Biophysical Journal*, vol. 87, pp. 2086-2097, Sep. 2004.

(56) References Cited

OTHER PUBLICATIONS

Algar, W. R. et al. "Quantum dots as donors in fluorescence resonance energy transfer for the bioanalysis of nucleic acids, proteins, and other biological molecules," *Anal Bioanal Chem*, vol. 391, pp. 1609-1618, Jul. 2008.

Anderson, B.N. et al. "Probing Solid-State Nanopores with Light for the Detection of Unlabeled Analytes," *ACS Nano*, 8(11), pp. 11836-11845, Nov. 2014.

Anderson, J. et al. "Incorporation of reporter-labeled nucleotides by DNA polymerases," *Biotechniques*, 38(2): 257-263, Feb. 2005.

Anderson, M. et al, "Next Generation DNA Sequencing and the Future of Genomic Medicine," *Genes*, vol. 1, pp. 38-69, Jun. 2010.

Augustin, M.A. et al. "Progress towards single-molecule sequencing: enzymatic synthesis of nucleotide-specifically labeled DNA," *Journal of Biotechnology*, 86(3), pp. 289-301, Apr. 2001.

Australian Patent Application No. 2010301128 filed May 13, 2010 in the name of Huber, Office Action dated Aug. 15, 2014.

Baker, L.A. et al., "A makeover for membranes," *Nature Nanotechnology*, vol. 3, pp. 73-74, Feb. 2008.

Bayley, H., "Sequencing single molecules of DNA," *Current Opinion in Chemical Biology*, 10(6), pp. 628-637, Dec. 2006.

Brakmann, S. "High-Density Labeling of DNA for Single Molecule Sequencing," *Methods in Molecular Biology*, vol. 283, pp. 137-144, Jun. 2004.

Brakmann, S. et al. "High-Density Labeling of DNA: Preparation and Characterization of the Target Material for Single-Molecule Sequencing," *Angew. Chem. Int. Ed.*, 40(8), pp. 1427-1429, Apr. 2001.

Branton, D. et al, "The potential and challenges of nanopore sequencing," *Nature Biotechnology*, 26(10), pp. 1146-1153, Oct. 2008.

Butler, T. Z. et al., "Single-molecule DNA detection with an engineered MspA protein nanopore," *Proceedings of the National Academy of Sciences*, 105(52), pp. 20647-20652, Dec. 30, 2008.

Carson, S. et al, "Challenges in DNA motion control and sequence readout using nanopore devices," *Nanotechnology*, 26(7), 14 pages, Feb. 2, 2015.

Chan, E. Y. et al. "DNA Mapping Using Microfluidic Stretching and Single-Molecule Detection of Fluorescent Site-Specific Tags," *Genome Research*, vol. 14, pp. 1137-1146, 2004.

Chan, W.C. et al. "Quantum Dot Bioconjugates for Ultrasensitive Nonisotopic Detection," *Science*, vol. 281, pp. 2016-2018, Sep. 25, 1998.

Chansin, et al. "Single-Molecule Spectroscopy Using Nanoporous Membranes," *Nano Letters*, vol. 7, No. 9; pp. 2901-2906, Aug. 25, 2007.

Chen, P. et al, "Atomic Layer Deposition to Fine-Tune the Surface Properties and Diameters of Fabricated Nanopores," *Nano Letters*, 4(7), pp. 1333-1337, Jun. 25, 2004.

Cherf, G. et al, "Automated forward and reverse ratcheting of DNA in a nanopore at 5-A precision," *Nat Biotechnol.*, 30(4), 6 pages, Feb. 14, 2012.

Clarke, J. et al, "Continuous base identification for single-molecule nanopore DNA sequencing," *Nature Nanotechnology*, 4(4), pp. 265-270, Apr. 2009.

Danelon, C. et al. "Fabrication and Functionalization of Nanochannels by Electron-Beam-Induced Silicon Oxide Deposition," *Langmuir*, vol. 22, pp. 10711-10715, Sep. 6, 2006.

Deamer, et al., "Characterization of Nucleic Acids by Nanopore Analysis," *Acc. Chem. Res.*, 35(10), pp. 817-825, 2002.

Deamer, et al., "Nanopores and nucleic acids: prospects for ultrarapid sequencing," *Trends in Biotechnology*, 18(4), abstract only (2 pages), Apr. 1, 2000.

Deblois, R. et al, "Counting and Sizing of Submicron Particles by the Resistive Pulse Technique," *Rev. Sci. Instruments*, 41(7), pp. 909-916, Jul. 1970.

Dekker, C. "Solid-state nanopores," *Nature Nanotechnology*, vol. 2, pp. 209-215, Apr. 2007.

Dennis, A.M. et al., "Quantum Dot—Fluorescent Protein Pairs as Novel Fluorescence Resonance Energy Transfer Probes," *Nano Lett.*, vol. 8, No. 5, pp. 1439-1445, Apr. 16, 2008, American Chemical Society.

Dorre, K. et al. "Highly efficient single molecule detection in microstructures," *Journal of Biotechnology*, 86(3), pp. 225-236, Apr. 2001.

Eid et al, "Real-time DNA sequencing from single polymerase molecules," *Science*, 323: 133-138, Supplemental Material, Jan. 2, 2009.

Eigen, M. et al. "Sorting single molecules: Application to diagnostics and evolutionary biotechnology," *Proc. Natl. Acad. Sci.*, vol. 91, pp. 5740-5747, Jun. 1994.

European Patent Application No. 10820963.6 filed May 13, 2010 in the name of Huber, Search Report and Opinion dated Dec. 20, 2013.

Foldes-Papp, Z. et al. "Fluorescent high-density labeling of DNA: error-free substitution for a normal nucleotide," *Journal of Biotechnology*, 86(3), pp. 237-253, Mar. 2001.

Fologea, et al. "Detecting Single Stranded DNA with a Solid State Nanopore," *Nano Letters*, 5 (10), abstract only, Aug. 31, 2005.

Fontes, A. et al. "Quantum Dots in Biomedical Research," Biomedical Engineering—Technical Applications in Medicine, Chapter 12, pp. 269-290, Sep. 6, 2012.

Freeman, J. et al, "Profiling the T-cell receptor beta-chain repertoire by massively parallel sequencing," Genome Research, vol. 19, pp. 1817-1824, Jun. 2009.

Galla et al. "Microfluidic carbon-blackened polydimethylsiloxane device with reduced ultra violet 1-4 background fluorescence for simultaneous two-color ultra violetlvisible-laser induced fluorescence detection in single cell analysis," *Biomicrofluidics* 6, pp. 014104-1 to 014104-10, Jan. 12, 2012.

Gierlich, J. et al, "Synthesis of Highly Modified DNA by a Combination of PCR with Alkyne-Bearing Triphosphates and Click Chemistry," *Chem. Eur. J.*, vol. 13, pp. 9486-9494, Nov. 16, 2007.

Giller, G. et al. "Incorporation of reporter molecule-labeled nucleotides by DNA polymerases. I. Chemical synthesis of various reporter group-labeled 2'- deoxyribonucleoside-5'-triphosphates," *Nucleic Acids Research*, 31(10), pp. 2630-2635, May 2003.

Grayson, A. et al, "A BioMEMS Review: MEMS Technology for Physiologically Integrated Devices," *Proceedings IEEE*, 92(1), pp. 6-21, Jan. 2004.

Gu, L. et al, "Single molecule sensing by nanopores and nanopore devices," *Analyst*, 135(3), pp. 441-451, 2010.

Gupta, et al., "Single-molecule DNA sequencing technologies for future genomic research," *Trends in Biotechnology*, 26(11), pp. 602-611, Nov. 1, 2008.

Ha, T. et al., "Probing the interaction between two single molecules: fluorescence resonance energy transfer between a single donor and a single acceptor," *Proc. Natl. Acad. Sci USA*, vol. 93, No. 13, pp. 6264-6268, Jun. 25, 1996.

Hall, A. R. et al. "Hybrid pore formation by directed insertion of alpha hemolysin into solid-state nanopores," *Nature Nanotechnology*, 5(12), pp. 874-877, Dec. 2010.

He, H. et al., "Single Nonblinking CdTe Quantum Dots Synthesized in Aqueous Thiopropionic Acid," *Angew. Chem. Int. Ed.* vol. 45, pp. 7588-7591, Oct. 2006.

Heins, E.A. et al., "Detecting Single Porphyrin Molecules in a Conically Shaped Synthetic Nanopore," *Nano Letters*, 5(9), pp. 1824-1829, Jul. 26, 2005.

Heins, E.A. et al., "Detecting Single Porphyrin Molecules in a Conically Shaped Synthetic Nanopore," *Nano Letters*, 5(9), pp. 1824-1829, Supporting Information, Jul. 26, 2005.

Heintzmann, R. et al., "Breaking the resolution limit in light microscopy," *Briefings in Functional Genomics and Proteomics*, 5(4), pp. 289-301, Dec. 2006.

Henriquez, R. et al, "The resurgence of Coulter counting for analyzing nanoscale objects," *The Analyst*, 129, pp. 478-482, 2004.

Holt, R. et al, "The new paradigm of flow cell sequencing," *Genome Research*, vol. 18, pp. 839-846, Jun. 2008.

Hsieh et al. "Effective Enhancement of Fluorescence Detection Efficiency in Protein MIcroarrayAssays: Application of a Highly

(56) References Cited

OTHER PUBLICATIONS

AuorInated Organosllane as the Blocking Agent on the Background Surface by a Facile Vapor-Phase Deposition Process," *Anal. Chem.*, 88:7908-7916, Aug. 25, 2009.

Huang, S. et al. "High-throughput optical sensing of nucleic acids in a nanopore array," *Nature Nanotechnology*, vol. 10, pp. 986-991, Aug. 2015.

Iqbal, S. M. et al., "Solid-state nanopore channels with DNA selectivity," *Nature Nanotechnology*, pp. 1-6, Apr. 1, 2007.

Ito, T. et al., "Observation of DNA transport through a single carbon nanotube channel using fluorescence microscopy," *Chem. Commun*, vol. 12, pp. 1482-1483, Aug. 2003.

Ivankin, A. et al. "Label-Free Optical Detection of Biomolecular Translocation through Nanopore Arrays," *ACS Nano*, 8(10), pp. 10774-10781, Sep. 2014.

Jagtiani, A. et al, "A label-free high throughput resistive-pulse sensor for simultaneous differentiation and measurement of multiple particle-laden analytes," *J. Micromech. Microeng.*, 16, pp. 1530-1539, Jun. 26, 2006.

Japanese Patent Application No. 2012-532069 filed May 13, 2010 in the name of Huber, Final Office Action dated Apr. 17, 2015.

Japanese Patent Application No. 2012-532069 filed May 13, 2010 in the name of Huber, Office Action dated Aug. 1, 2014.

Japanese Patent Application No. 2014-224165 filed May 13, 2010 in the name of Huber, Office Action dated Oct. 15, 2015.

Johansson, MK et al. "Choosing Reporter-Quencher Pairs for Efficient Quenching Through Formation of Intramolecular Dimers," *Methods in Molecular Biology*, vol. 335:2, pp. 17-29, 2006.

Johansson, MK et al. "Intramolecular Dimers: A New Design Strategy for Fluorescence-Quenched Probes," *Chem. Eur. J.*, 9, 3466-3471, Jul. 2003.

Kang, X. et al., "A storable encapsulated bilayer chip containing a single protein nanopore," *J Am Chem Soc.* vol. 129, No. 15, pp. 4701-4705, Mar. 22, 2007.

Kasianowicz, J.J. et al., "Characterization of Individual Polynucleotide Molecules Using a Membrane Channel," *Proc. Natl. Acad. Sci USA*, vol. 93, pp. 13770-13773, Nov. 1996.

Keyser, U. F. "Controlling molecular transport through nanopores," *Journal of the Royal Society Interface*,10 page, Oct. 7, 2011.

Kircher, M. et al, "High-throughput DNA sequencing-concepts and limitations," *Bioessays*, vol. 32, pp. 524-536, Jun. 2010.

Kleefen, A. et al. "Multiplexed Parallel Single Transport Recordings on Nanopore Arrays," *Nano Letters*, vol. 10, pp. 5080-5087, Oct. 27, 2010.

Kocer, A. et al. "Nanopore sensors: From hybrid to abiotic systems," *Biosensors and Bioelectronics*, vol. 38, 10 pages, Jun. 2012.

Kolb, H. et al, "Click Chemistry: Diverse Chemical Function from a Few Good Reactions," *Angew. Chem. Int. Ed.*, vol. 40, pp. 2005-2021, Jun. 1, 2001.

Kristensen, V. N. et al., "High-Throughput Methods for Detection of Genetic Variation," *BioTechniques*, 30(2), pp. 318-332, Feb. 2001.

Lazlo, A.H. et al, "Decoding long nanopore sequencing reads of natural DNA," *Nature Biotechnology*, 32(8): 829-834 and Supplemental Materials, Jun. 25, 2014.

Lee et al. "High aspect ratio polymer microstructures and cantilevers for bIoMEMS using low energy ion beam and photolithography," *Sensors and Actuators A*, 71:144-149, Apr. 1998.

Lerner, H. et al, "Prospects for the Use of Next-Generation Sequencing Methods in Ornithology," *The Auk*, 127(1), pp. 4-15, Feb. 2010.

Levene et al, "Zero mode waveguide for single-molecule analysis in high concentration," *Science*, 299: 682-686, Jan. 31, 2003.

Li et al., "DNA Molecules and Configurations in a Solid-State Nanopore Microscope," *Nat. Mater*, vol. 2, pp. 611-615, Sep. 2003.

Li, J. et al., "Nanoscale Ion Beam Sculpting," *Nature*, vol. 412, pp. 166-169, Jul. 12, 2001.

Lo, C.J. et al. "Fabrication of symmetric sub-5 nm nanopores using focused ion and electron beams," *Nanotechnology*, vol. 17, No. 13, pp. 3264-3267, Jul. 2006.

Lu et al. "Parylene Background Fluorescence Study for Biomems Applications," *Transducers*, pp. 176-179, Jun. 21-25, 2009.

Luan et al., "Slowing and controlling the translocation of DNA in a solid-state nanopore," *Nanoscale*, 4(4): 1068-1077, Feb. 21, 2012.

Maitra, R. D. et al. "Recent advances in nanopore sequencing," *Electrophoresis*, vol. 33, pp. 3418-3428, Dec. 2012.

Manrao, E. et al. "Reading DNA at single-nucleotide resolution with a mutant MspA nanopore and phi29 DNA polymerase," *Nat Biotechnol*, 30(4), 6 pages, Mar. 25, 2012.

Marras, S. "Interactive Fluorophore and Quencher Pairs for Labeling Fluorescent Nucleic Acid Hybridization Probes," *Mol Biotechnol*, vol. 38, 247-255, Mar. 2008.

Marras, S. "Selection of Fluorophore and Quencher Pairs for Fluorescent Nucleic Acid Hybridization Probes," *Methods in Molecular Biology*, vol. 335, 3-16, 2006.

McNally, et al. "Optical recognition of converted DNA nucleotides for single•molecule DNA sequencing using nanopore arrays," *Nano Letters*, vol. 10, No. 6; pp. 2237-2244, Jun. 9, 2010.

Meagher, R. J. et al. "Free-solution electrophoresis of DNA modified with drag-tags at both ends," *Electrophoresis*,vol. 27, pp. 1702-1712, May 2006.

Meagher, R. J. et al. "Sequencing of DNA by Free-Solution Capillary Electrophoresis Using a Genetically Engineered Protein Polymer Drag-Tag," *Anal. Chem.*, vol. 80, pp. 2842-2848, Apr. 15, 2008.

Medintz, I.L. et al. "A fluorescence resonance energy transfer-derived structure of a quantum dot-protein bioconjugate nonassembly," *PNAS*, 101(26), pp. 9612-9617, Jun. 29, 2004.

Medintz, I.L. et al. "Quantum dot bioconjugates for imaging, labelling and sensing," *Nature Materials*, vol. 4, 435-446, Jun. 2005.

Meller, A. et al., "Rapid nanopore discrimination between single polynucleotide molecules," *The National Academy of Sciences*, 7 pages, Feb. 1, 2000.

Meller, A. et al., "Voltage-Driven DNA Translocations through a Nanopore," *Phys. Rev. Lett.* 86(15), pp. 3435-3438, Apr. 2001.

Meller, et al., "Single Molecule Measurements of DNA Transport through a Nanopore," *Electrophoresis*,vol. 23, pp. 2583-2591, Aug. 2002.

Metzker, M. "Sequencing technologies—the next generation," *Nature Review Genetics*, vol. 11, pp. 31-46, Jan. 2010.

Mir, K., "Ultrasensitive RNA profiling: Counting single molecules on microarrays," *Genome Research*,16:1195-1197, Oct. 2006.

Moerner, W.E. et al. "Methods of single-molecule fluorescence spectroscopy and microscopy," *Review of Scientific Instruments*, 74(8), pp. 3597-3619, Aug. 2003.

Nakane, J. et al, "Evaluation of nanopores as candidates for electronic analyte dectection," *Electrophoresis*, vol. 23, pp. 2592-2601, Aug. 20, 2002.

Nakane, J. et al, "Nanopore sensors for nucleic acid analysis," *J. Phys. Condens. Matter*, Matter 15, pp. R1365-R1393, Aug. 1, 2003.

Paul, N. et al. "PCR incorporation of modified dNTPs: the substrate properties of biotinylated dNTPs," *Biotechniques*, 48(4), 333-334, Apr. 2010.

PCT International Patent Application No. PCT/US2010/034809 filed May 13, 2010 in the name of Quantapore, Inc., International Search Report and Written Opinion dated Feb. 6, 2014.

PCT International Patent Application No. PCT/US2010/034809 filed May 13, 2010 in the name of Quantapore, Inc., International Search Report and Written Opinion dated Sep. 13, 2010.

PCT International Patent Application No. PCT/US2011/54365 filed Sep. 30, 2011 in the name of Quantapore, Inc., International Search Report and Written Opinion dated Apr. 25, 2012.

PCT International Patent Application No. PCT/US2013/067126 filed Oct. 28, 2013 in the name of Quantapore, Inc., International Search Report and Written Opinion dated May 6, 2014.

PCT International Patent Application No. PCT/US2014/039444 filed May 23, 2014 in the name of Quantapore, Inc., International Search Report and Written Opinion dated Dec. 3, 2014.

PCT International Patent Application No. PCT/US2015/054756 filed Oct. 8, 2015 in the name of Quantapore, Inc., International Search Report and Written Opinion dated Jan. 6, 2016.

Ramachandran, G. et al. "Current bursts in lipid bilayers initiated by colloidal quantum dots," *Applied Physics Letter*, 86:083901-1 to 083901-3, Feb. 17, 2005.

(56) References Cited

OTHER PUBLICATIONS

Ramsay, N. et al. "CyDNA: Synthesis and Replication of Highly Cy-Dye Substituted DNA by an Evolved Polymerase," *J. Am. Chem. Soc.*, vol. 132, 5096-5104, Mar. 2010.
Randolph, JB et al. "Stability, specificity and fluorescence brightness of multiply-labeled fluorescent DNA probes," *Nucleic Acids Research*, 25(14) 2923-2929, May 1997.
Rasnik, I. et al., "Nonblinking and long-lasting single-molecule fluorescence imaging," *Nature Methods*, 3(11), pp. 891-893, Nov. 2006.
Reed, M.A. "Quantum Dots," *Scientific American*, pp. 118-123, Jan. 1993.
Resch-Genger, U. et al. "Quantum dots versus organic dyes as fluorescent labels," *Nature Methods*,5(9), pp. 763-775, Sep. 2008.
Rhee, M. et al., "Nanopore Sequencing Technology: Nanopore Preparations," *Trends in Biotechnology*, vol. 25, No. 4, pp. 174-181, Apr. 2007.
Rhee, M. et al., "Nanopore Sequencing Technology: research trends and applications," *Trends in Biotechnology*, vol. 24, No. 12, pp. 580-586, Dec. 2006.
Roy et al. "A practical guide to single molecule FRET," *Nature Methods*, 5(6): 507-516, Jun. 2008.
Sabanayagam, C.R. et al., "Long time scale blinking kinetics of cyanine fluorophores conjugated to DNA and its effect on Forster resonance energy transfer," *J. Chem. Phys.*, 123(22), pp. 224708-1 to 224708-7, Dec. 2005.
Sanger, F. et al., "DNA Sequencing with Chain-Terminating Inhibitors," *Proc. Natl. Acad. Sci. USA*, vol. 74, No. 12, pp. 5463-5467, Dec. 1977.
Sauer, M. et al. "Single molecule DNA sequencing in submicrometer channels: state of the art and future prospects," *Journal of Biotechnology*, 86(3), 181-201, Apr. 2001.
Sawafta, F. et al., "Solid-state nanopores and nanopore arrays optimized for optical detection," *Nanoscale*, DOI: 10.1039/c4nr00305e, vol. 6 pp. 6991-6996, May 2014.
Schumacher, S. et al, "Highly-integrated lab-on-chip system for point-of-care multiparameter analysis," *Lab on a Chip*, 12(3), pp. 464-473, Feb. 7, 2012.
Seela, F. et al. "Fluorescent DNA: the development of 7-deazapurine nucleoside triphosphates applicable for sequencing at the single molecule level," *Journal of Biotechnology*, 86(3), 269-279, Apr. 2001.
Shaffer, C., "Next generation sequencing outpaces expectations," *Nature Biotechnology*, vol. 25, p. 149, Feb. 2007.
Shi, L. et al. "Luminescent Quantum Dots Fluorescence Resonance Energy Transfer-Based Probes for Enzymatic Activity and Enzyme Inhibitors," *Anal. Chem*, 79(1), pp. 208-214, Jan. 1, 2007.
Singer, A. et al, "DNA sequencing by nanopore-induced photon emission," *Methods in Molecular Biology*, vol. 870, pp. 99-114 Feb. 29, 2012.
Smolina, I.V. et al. "High-density fluorescently labeled rolling-circle amplicons for DNA diagnostics," *Analytical Biochemistry*, 347: 152-155, Jun. 21, 2005.
Song, L. et al., "Structure of Staphylococcal alpha-hemolysin, a heptameric transmembrane protein," *Science*, vol. 274, No. 5294, pp. 1859-1866, Dec. 13, 1996.
Soni, et al. "Progress toward Ultrafast DNA Sequencing Using Solid•State Nanopores," *Clinical Chemistry*, vol. 53, No. 11; pp. 1996-2001, Oct. 2007.
Soni, G. V. et al. "Synchronous optical and electrical detection of biomolecules traversing through solid-state nanopores," *Review of Scientific Instruments*, pp. 014301-1-014301-7, published online Jan. 19, 2010.
Stephan, J. et al. "Towards a general procedure for sequencing single DNA molecules," *Journal of Biotechnology*, 86(3) 255-267, Apr. 2001.
Storm, A. J. et al. "Fabrication of solid-state nanopores with single-nanometre precision," *Nature Materials*, vol. 2, pp. 537-540, Aug. 2003.
Stryer, L., "Fluorescence Energy Transfer as a Spectroscopic Ruler," *Annual Review of Biochemistry*, vol. 47, pp. 819-846, Jul. 1978.
Tasara, T. et al. "Incorporation of reporter molecule-labeled nucleotides by DNA polymerases. II. High-density labeling of natural DNA," *Nucleic Acids Research*, 31(10), 2636-2646, May 2003.
Telenius, H. et al., "Degenerate oligonucleotide-primed PCR: General amplification of target DNA by a single degenerate primer," *Genomics*, vol. 13, No. 3, pp. 718-725, Jul. 1992.
Thompson, J. F. et al. "The properties and applications of single-molecule DNA sequencing," *Genome Biology*, 12(217), 10 pages, Feb. 24, 2011.
Timp, W., et al, "DNA base-calling form a nanopore using a Viterbi algorithm," *Biophysical J.*, vol. 102, pp. L37-L39, May 2012.
Tucker, T. et al, "Massively Parallel Sequencing: The Next Big Thing in Genetice Medicine," *Am. J. Human Genet.*, vol. 85, pp. 142-154, Aug. 2009.
Turner, E. et al, "Methods for Genomic Partitioning," *Annual Review of Genomics and Human Genetics*, vol. 10, pp. 263-284, Sep. 2009.
U.S. Appl. No. 13/426,515, filed Mar. 21, 2012 in the name of Huber, Non-final Office Action dated Dec. 2, 2013.
U.S. Appl. No. 13/662,532, filed Oct. 28, 2012 in the name of Huber, Final Office Action dated Mar. 17, 2015.
U.S. Appl. No. 13/662,532, filed Oct. 28, 2012 in the name of Huber, Non-final Office Action dated Aug. 7, 2014.
U.S. Appl. No. 13/662,532, filed Oct. 28, 2012 in the name of Huber, Non-final Office Action dated Dec. 20, 2013.
U.S. Appl. No. 14/018,376, filed Sep. 4, 2013 in the name of Huber, Final Office Action dated Sep. 24, 2015.
U.S. Appl. No. 14/018,376, filed Sep. 4, 2013 in the name of Huber, Non-final Office Action dated Mar. 3, 2015.
U.S. Appl. No. 14/285,474, filed May 22, 2014 in the name of Huber, Non-final Office Action dated Apr. 30, 2015.
U.S. Appl. No. 14/285,474, filed May 22, 2014 in the name of Huber, Notice of Allowance dated Nov. 20, 2015.
U.S. Appl. No. 61/168,431, filed Apr. 10, 2009.
Venkatesan, B. M. et al. "Lipid bilayer coated Al2O3 naopore sensors: towards a hybrid biological solid-state nanopore," *Biomed Microdevices*, 13(4), 21 pages, Sep. 18, 2011.
Venkatesan, B. M. et al. "Nanopore sensors for nucleic acid analysis," *Nature Nanotechnology*,vol. 6, pp. 615-624, Oct. 2011.
Vercoutere, W. et al., "Rapid discrimination among individual DNA hairpin molecules at single-nucleotide resolution using an ion channel," *Nature Biotechnology*, vol. 19, pp. 248-252, Mar. 2001.
Voelkerding, K. et al, "Next-Generation Sequencing: From Basic Research to Diagnostic," *Clinical Chemistry*, 55:4, pp. 641-658, Apr. 2009.
Walker, B. et al. "Key Residues for Membrane Binding, Oligomerization, and Pore Forming Activity of Staphylococcal alpha-Hemolysin Identified by Cysteine Scanning Mutagenesis and Targeted Chemical Modification," *Journal of Biological Chemistry*, 270(39), pp. 23065-23071, Sep. 29, 1995.
Wang, H. et al., "Nanopores with a spark for single-molecule detection," *Nature Biotechnology*, vol. 19, pp. 622-633, Jul. 2001.
Wanunu, M. et al. "Chemically Modified Solid-State Nanopores," *Nano Letters*, 7(6), pp. 1580-1585, May 16, 2007.
Wanunu, M. et al."Nanopores: A journey towards DNA sequencing," *Physics of Life Reviews*, vol. 9, pp. 125-158, Jun. 2012.
White et al., "Single Ion-Channel Recordings Using Glass Nanopore Membranes," *J. Amer. Chem. Soc.*, 129:11766-11775, Sep. 5, 2007.
Won, J. et al. "Protein polymer drag-tags for DNA separations by end-labeled free solution electrophoresis," *Electrophoresis*, vol. 26, pp. 2138-2148, Jun. 2005.
Wu, X. et al, "Microfluidic differential resistive pulse sensors," *Electrophoresis*, 29(13), pp. 2754-2759, Jun. 2008.
Xu, et al. "Perspectives and Challenges of Emerging Single-Molecule DNA Sequencing Technologies," *SMALL*, 5(53), pp. 2638-2649, Dec. 4, 2009.
Yan, X. et al, "Parallel Fabrication of Sub-50-nm Uniformly Sized Nanaparticles by Deposition through a Patterned Silicon Nitride Nanostencil," *Nano Letters*, 5(6), pp. 1129-1134, Jul. 2005.

(56) References Cited

OTHER PUBLICATIONS

Yang, J. et al. "Rapid and precise scanning helium ion microscope milling of solid-state nanopores for biomolecule detection," *Nanotechnology*, vol. 22, 6 pages, Jun. 10, 2011.

Yu, H. et al. "Cyanine dye dUTP analogs for enzymatic labeling of DNA probes," *Nucleic Acids Research*, 22(15), 3226-3232, Apr. 1994.

Yu, Y. et al. "Facile preparation of non-self-quenching fluorescent DNA strands with the degree of labeling up to the theoretic limit," *Chem. Commun.*, vol. 48, 6360-6362, May 2012.

Zhang, L. et al., "Whole genome amplification from a single cell: implications for genetic analysis," *Proc. Natl. Acad. Sci. USA*, vol. 89, No. 13, pp. 5847-5851, Jul. 1, 1992.

Zhe, J. et al, "A micromachined high throughput Coulter counter for bioparticle detection and counting," *J. Micromech. Microeng.*, vol. 17, pp. 304-313, Jan. 11, 2007.

Zheng, S. et al. "Parallel analysis of biomolecules on a microfabricated capillary array chip," *Electrophoresis*, vol. 26, abstract only, Mar. 2006.

Zhu, Z. et al. "Directly labeled DNA probes using fluorescent nucleotides with different length linkers," *Nucleic Acids Research*, 22(16), 3418-3422, Aug. 1994.

PCT International Patent Application No. PCT/US2017/038813 filed Jun. 22, 2017 in the name of Quantapore, Inc., International Search Report and Written Opinion dated Sep. 29, 2017.

Chen, C. "Plasmonic Nanopores for Direct Molecular Identification," Dissertation presented in partial fulfilment of the requirements for the degree of Doctor of Science, 190 pages, Katholieke Universiteit Leuven, May 2011.

\* cited by examiner

↓ Extend
(707)

Three Labels:

720
○◆●●◆◆◆○○○●●◆◆◆◆●◆◆●◆●◆○
TGGCAAATTTCCAAAGGGGCAGCAT
ACCGTTTAAAGGTTTCCCCGTCGTA

722
◆○◆●○◆●●●●○○○◆◆◆◆○○○●●◆
ATGCTGCCCCTTTGGAAATTTGCCA
TACGACGGGGAAACCTTTAAACGGT

↓ Determine Optical Signatures
(709)

From time reverse optical
          signature of 722:    5'- pCCpTTTpppppTTTCCCCpTCpTp From optical signature 720:    3'- TppCpppTTTCCppppppppCppCpT

Fig. 7B

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: The sequence is synthesized.

<400> SEQUENCE: 1
accgtttaaa ggtttccccg tcgta                                     25

<210> SEQ ID NO 2
<211> LENGTH: 25
<212> TYPE: DNA
<213> ORGANISM: Artificial Sequence
<220> FEATURE:
<223> OTHER INFORMATION: The sequence is synthesized.

<400> SEQUENCE: 2
tacgacgggg aaacctttaa acggt                                     25
```

OPTICALLY BASED NANOPORE SEQUENCING

CROSS-REFERENCE TO RELATED APPLICATIONS

This application is a U.S. national application filed under 35 U.S.C. 371 to PCT International Application No. PCT/US2017/038813 filed Jun. 22, 2017, which claims benefit of priority to U.S. Provisional Patent Application No. 62/358,552, filed on Jul. 5, 2016, the content of each of which is incorporated herein by reference in its entirety.

BACKGROUND

Nanopore sequencing has been proposed as an approach to overcome a host of challenges in current DNA sequencing technologies, including reduction of per-run sequencing cost, simplification of sample preparation, reduction of run times, increasing sequence read lengths, providing real-time sample analysis, and the like. However, polymer analysis, such as DNA analysis, with nanopores has its own set of technical difficulties, such as, reliable nanostructure fabrication, control of DNA translocation rates, unambiguous nucleotide discrimination, detection and processing of signals from large arrays of nanoscale sensors, and so on, e.g. Branton et al, Nature Biotechnology, 26(10): 1146-1153 (2008).

Optical detection of nucleotides has been proposed as a potential solution to some of the technical difficulties in the field of nanopore sequencing, such as, for example, the difficulty of collecting independent signals from large arrays of nanopores. However, there are numerous challenges to implementing optical approaches, in particular the difficulty of measuring optical signals from single molecular labels on translocating polynucleotides against a significant background of optical noise. Measurements of fluorescent signals from single molecules have been made and fluorescent signals have been optimized by aligning fluorescent absorption dipoles of the molecules with the direction of the electrical field vector of the excitation light, e.g. Lakowicz, Principles of Fluorescence Spectroscopy, Third Edition (Springer, 2006); Moerner et al, Review of Scientific Instruments, 74(8): 3597-3619 (2003); Michalet et al, Ann. Rev. Biophys. Biomol. Struct., 32: 161-182 (2003), but the techniques used have not as yet been applied to nanopore sequencing.

In view of the above, the challenge of low signal-to-noise ratios of optical signals in nanopore sequencing could be addressed if methods were available for aligning or orienting fluorescent labels for optimized signal generation and detection.

SUMMARY OF THE INVENTION

The present invention is directed to methods and devices for polynucleotide analysis using nanopores to align and/or orient fluorescent absorption dipoles for preferential excitation or quiescence.

In one aspect, the invention is directed to methods of analyzing a polynucleotide comprising the steps: (a) directing to a nanopore an excitation beam having a predetermined polarization state; (b) translocating a polynucleotide through the nanopore, wherein nucleotides of the polynucleotide are labeled with fluorescent labels having absorption dipoles and wherein the nanopore spatially orients the fluorescent labels so that during translocation the absorption dipoles are substantially unresponsive to the excitation beam; (c) detecting changes in fluorescent signals generated by the fluorescent labels as nucleotides with fluorescent labels exit the nanopore and absorption dipoles thereof become responsive to excitation by the excitation beam with the predetermined polarization state; and (d) identifying nucleotides exiting the nanopore from the changes in fluorescent signals.

The present invention advantageously overcomes the above problems in the field of optically based nanopore sequencing by using nanopore to spatially constrain and orient absorption dipoles of fluorescent labels. These and other advantages of the present invention are exemplified in a number of implementations and applications, some of which are summarized below and throughout the specification.

BRIEF DESCRIPTION OF THE DRAWINGS

FIGS. 7A-7C illustrate embodiments employing two and three fluorescent labels.

DETAILED DESCRIPTION OF THE INVENTION

Figure 1A:
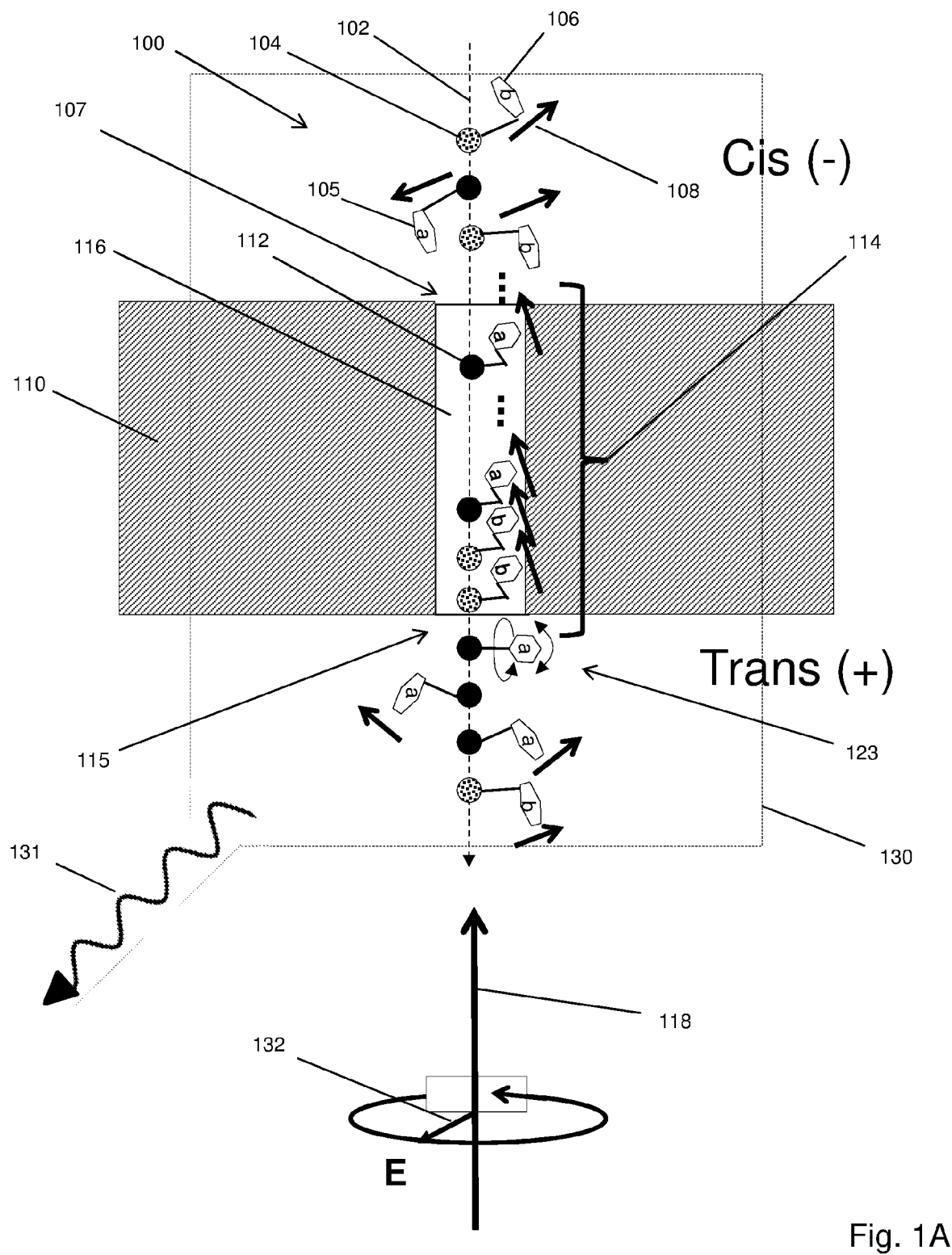
FIGS. 1A-1B illustrates exemplary embodiments of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention. For example, particular nanopore types and numbers, particular labels, FRET pairs, detection schemes, fabrication approaches of the invention are shown for purposes of illustration. It should be appreciated, however, that the disclosure is not intended to be limiting in this respect, as other types of nanopores, arrays of nanopores, and other fabrication technologies may be utilized to implement various aspects of the systems discussed herein. Guidance for aspects of the invention is found in many available references and treatises well known to those with ordinary skill in the art, including, for example, Cao, Nanostructures & Nanomaterials (Imperial College Press, 2004); Levinson, Principles of Lithography, Second Edition (SPIE Press, 2005); Doering and Nishi, Editors, Handbook of Semiconductor Manufacturing Technology, Second Edition (CRC Press, 2007); Sawyer et al, Electrochemistry for Chemists, $2^{nd}$ edition (Wiley Interscience, 1995); Bard and Faulkner, Electrochemical Methods: Fundamentals and Applications, $2^{nd}$ edition (Wiley, 2000); Lakowicz, Principles of Fluorescence Spectroscopy, $3^{rd}$ edition (Springer, 2006); Hermanson, Bioconjugate Techniques, Second Edition (Academic Press, 2008); and the like, which relevant parts are hereby incorporated by reference.

In one aspect, the invention is directed to methods and devices for analyzing polynucleotides, such as DNA, RNA, and the like, using nanopores and optical detection. In one aspect, the invention employs nanopores selected not only for constraining nucleotides to move in a single file manner through a detection zone, but also for orienting fluorescent labels during translocation so that their absorption dipoles are unresponsive to an excitation beam with a predetermined polarization state, as illustrated schematically in FIG. 1A. Whenever nucleotides emerge from the nanopore, their fluorescent labels gain freedom of rotation and movement so that they can be excited by the excitation beam to produce a jump in emitted fluorescence, which may then be used to identify the emerging nucleotide. In some embodiments, a predetermined polarization state of an excitation beam is one in which the beam's electrical vector is substantially orthogonal to the absorption dipoles of a particular set of nucleotide labels. In some embodiments, the predetermined polarization state may include circular polarization; in other embodiments, the predetermined polarization state may include a linear polarization. In further embodiments, the predetermined polarization state may include the number of excitation beams used and their angles of incidence with respect to the nanopore (e.g., the axis of the bore of the nanopore). In some embodiments, more than one excitation beams may be employed each with its own predetermined polarization state. In some embodiments, a predetermined polarization state has an electrical field vector which is substantially aligned with the absorption dipoles of the fluorescent labels in the nanopore. In other embodiments, a predetermined polarization state has an electrical field vector which is substantially orthogonal to the absorption dipoles of the fluorescent labels in the nanopore. In some embodiments, a predetermined polarization state has an electrical field vector which is maximally aligned with the absorption dipoles of the fluorescent labels in the nanopore. In other embodiments, a predetermined polarization state has an electrical field vector which is maximally orthogonal to the absorption dipoles of the fluorescent labels in the nanopore.

In the above aspect, the particular set of nucleotide labels are those attached to nucleotides inside of the nanopore whose absorption dipoles have been constrained to a restricted orientation, rendering the labels substantially unresponsive to the excitation beam, whereas labels adjacent to the entrance and/or the exit of the nanopore are not so constrained and are responsive to excitation by light having the predetermined polarization state. In some embodiments, the above aspect of the invention may be implemented with the following steps: (a) directing to a nanopore an excitation beam having a predetermined polarization state; (b) translocating a polynucleotide through the nanopore, wherein nucleotides of the polynucleotide are labeled with fluorescent labels having absorption dipoles and wherein the nanopore spatially orients the fluorescent labels so that during translocation the adsorption dipoles are substantially unresponsive to the excitation beam; (c) detecting changes in fluorescent signals generated by the fluorescent labels as nucleotides with fluorescent labels exit the nanopore and absorption dipoles thereof become responsive to excitation by the excitation beam with the predetermined polarization state; and (d) identifying nucleotides exiting the nanopore from the changes in fluorescent signals. In some embodiments, the predetermined polarization state is circular polarization wherein the plane containing the electrical field vector of the excitation beam is substantially perpendicular to the axis of the nanopore, or substantially perpendicular to the direction of translocation through the nanopore. In some embodiments, the change in fluorescent signal as a nucleotide exits the nanopore is an increase in magnitude of fluorescence due to the fluorescent label becoming capable of excitation and emission when its absorption dipole becomes mobile. In some embodiments, such changes in fluorescence level occur within a period of less than 1 msec, or less than 0.1 msec, or less than 0.01 msec. In some embodiments, such changes in fluorescence levels persist until the fluorescent label moves out of the detection volume, or is quenched by a label of an adjacent nucleotide, or is bleached. In some embodiments, such changes persist for at least 0.01 msec, or at least 0.1 msec, or at least 0.5 msec.

Figure 1B:
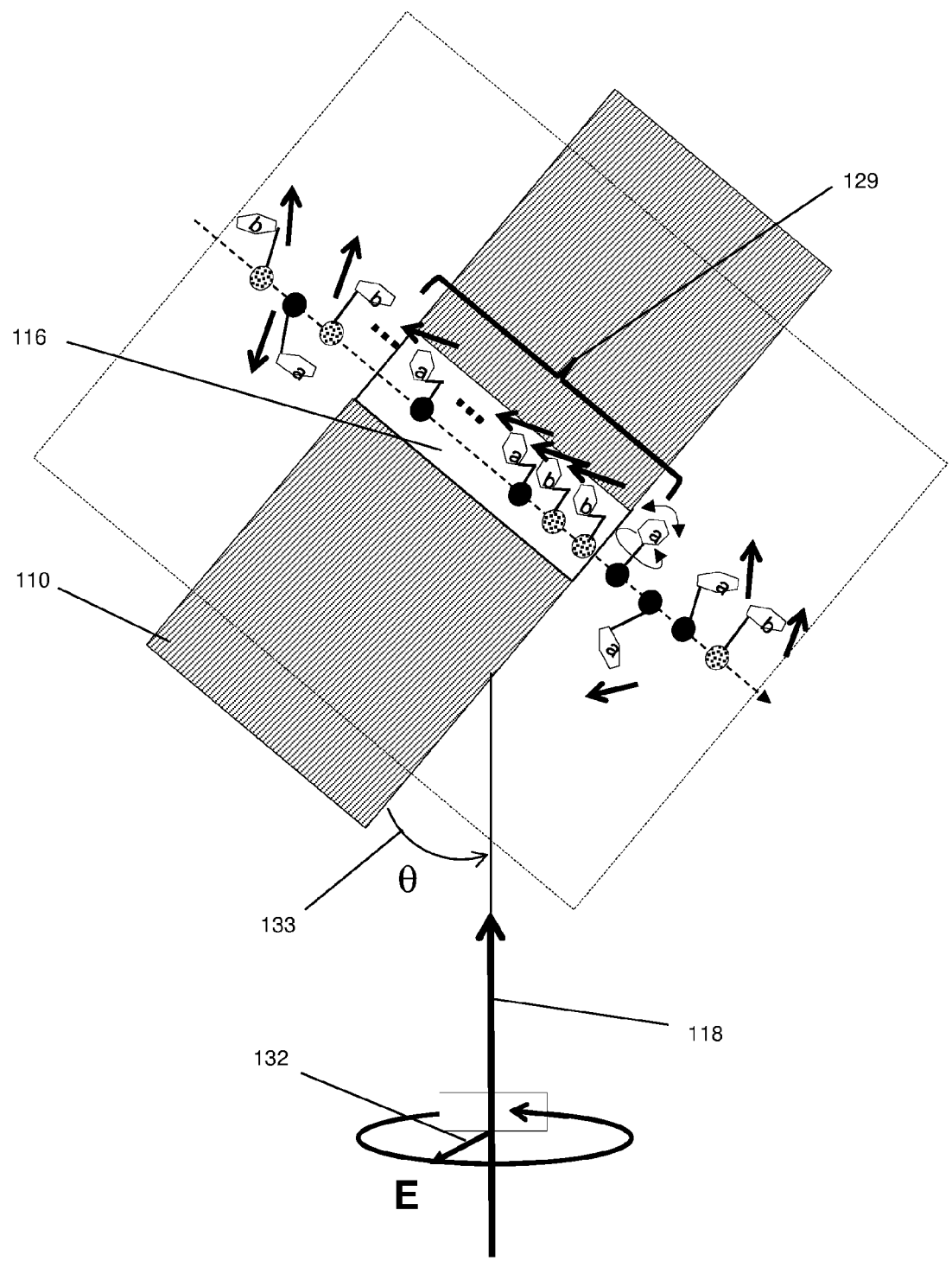

In another aspect, the invention employs nanopores as above for constraining nucleotides to move in a single file manner through a detection zone, but also for orienting fluorescent labels during translocation so that their absorption dipoles are maximally responsive to an excitation beam with a predetermined polarization state, as illustrated schematically in FIG. 1B. In this aspect, whenever a nucleotide is in the nanopore, its fluorescent label generates an optical signal indicative of the nucleotide. In the embodiments of FIG. 1B, alignment of the polarization of the excitation beam and the oriented absorption dipoles of fluorescent labels within the nanopore (129) is achieved by directing excitation beam (118) to membrane (110) containing nanopore (116) at an angle, θ (133), which is selected so that the absorption dipoles substantially lie in the plane defined by electrical field vector (132). Because a plurality of labeled nucleotides are expected to occupy a nanopore during translocation (for example, 3 to 10, depending on the particular nanopore used), a collected optical signal may comprise individual optical signals from labels of some or all nucleotides in the nanopore and, in some cases, optical signals from labels of nucleotides outside of the nanopore. Thus, in such embodiments, an additional step or steps for separating or otherwise analyzing the detected signal may be required to obtain nucleotide identities from such mixed optical signals, as described more fully below.

In some embodiments of both of the above aspects, mutually and self-quenching fluorescent labels may be used to reduce undesired optical signals, which, in turn, reduces the difficulties of identifying individual nucleotides from mixed optical signals. As described more fully below, in such embodiments, labels of adjacent nucleotides are selected so that in free solution outside of a nanopore, labels of adjacent nucleotides quench fluorescent emissions from one another.

Exemplary embodiments of the initially described aspect are illustrated in FIGS. 1A-1B, 2 and 3. In FIG. 1A, single stranded polynucleotide (100) is shown translocating through nanopore (116) that is formed in membrane (110) from a cis (−) chamber to a trans (+) chamber. Polynucleotides analyzed by methods of the invention may be single stranded or double stranded. For example, in some embodiments, labeled single stranded polynucleotides are generated by extending in the presence of labeled precursors a 5'-tailed primer on a template (which may be a component of a nucleic acid sample from a source of interest), after which the 5'-tail inserts into a nanopore and the labeled strand unzips from the template strand in the course of translocation. In other embodiments, the double stranded extension product may be translocated though a nanopore intact, without unzipping. In the latter embodiment, a nanopore with a larger diameter may be required than that of a nanopore used with a single stranded polynucleotide analyte.

Nucleotides of polynucleotide (100) are illustrated as filled (e.g. 112) or patterned (e.g. 104) circles along backbone (102) illustrated as a dashed arrow. Filled circles represent one kind of nucleotide (e.g. A) whereas pattern filled circles represent a different kind of nucleotide (e.g., C, G or T, or the same label may be attached to all three in a 2-label embodiment). Each nucleotide has a fluorescent label (e.g. 106) that is capable of generating a distinct fluorescent signal indicative of the nucleotide. In this case, two fluorescent labels are displayed, "a" (e.g. 105) attached to nucleotides represented by filled circles (e.g., 112) and "b" (e.g. 106) attached to nucleotides represented by patterned circles (e.g. 104), which represent fluorescent labels that generate distinguishable optical signals. Fluorescent labels, "a" and "b", each have absorption dipoles which define directions in which the labels efficiently absorb light energy from an excitation beam with a co-aligned electrical field vector. In one aspect, the invention includes a recognition and appreciation by the inventor that fluorescent absorption dipoles and the polarization state of an excitation beam may be configured or oriented by a nanopore to optimize the detection of single fluorescent labels in the context of optically based nanopore sequencing. In accordance with embodiments of this aspect, nanopore (116) is dimensioned so that absorption dipoles of fluorescent labels, such as labels "a" and "b", inside nanopore (116) are oriented in a common direction (114) that is substantially orthogonal to the polarization state of light from excitation beam (118), which is shown as being circularly polarized with electrical field vector (132) rotating in a plane orthogonal to the axis of nanopore (116). That is, light from excitation beam (118) may be circularly polarized such that the electrical field vector circulates in a plane perpendicular to the translocation direction (e.g. defined by line 102) of polynucleotide (100). In other embodiments, excitation beams with different polarization states may be employed.

Without intending to be limited by the following, it is believed that the orientation of dipoles takes place because the diameter of a nanopore (such as, 116) provides less space for free rotation of fluorescent labels attached to bases and that labels of a translocating polynucleotide are therefore spatially constrained to a particular orientation to permit passage through the nanopore (which orientation renders them unresponsive to excitation by an excitation beam with a predetermined polarization state in the above aspect). Whenever labeled nucleotides enter (107) or exit (115) nanopore (116), optical signals being detected are affected, typically manifested by a decrease or increase (respectively) of optical signal intensity related to the wavelength characteristics of the nucleotide labels, and depending on features of particular embodiments, such as, the details of the optical system (e.g. epi-illumination, TIR, etc.), direction of the excitation beam, the extent or volume of a detection zone (e.g. 130), the type of polarization employed, the presence or absence of mutual or self-quenching labels, the propensity of labels to bleach, and so on. In some embodiments, in which a detection zone encompasses both entrance (107) and exit (115) of nanopore (116), transitions between a free-rotation state to an oriented state (upon entering nanopore (116) and an oriented state to a free-rotation state (upon exiting nanopore (116 and 123) are reflected by jumps in optical signal intensity (131) collected from detection zone (130). The distinguishing characteristics of the components of an optical signal contributing to such jumps may be used to identify nucleotides entering and/or exiting nanopore (116). In some embodiments, features are selected (for example, detection zone or signal collection volume) so that jumps, i.e. sudden or fast changes in signal intensity, are due substantially only to labeled nucleotides exiting nanopore (116).

Figure 2:
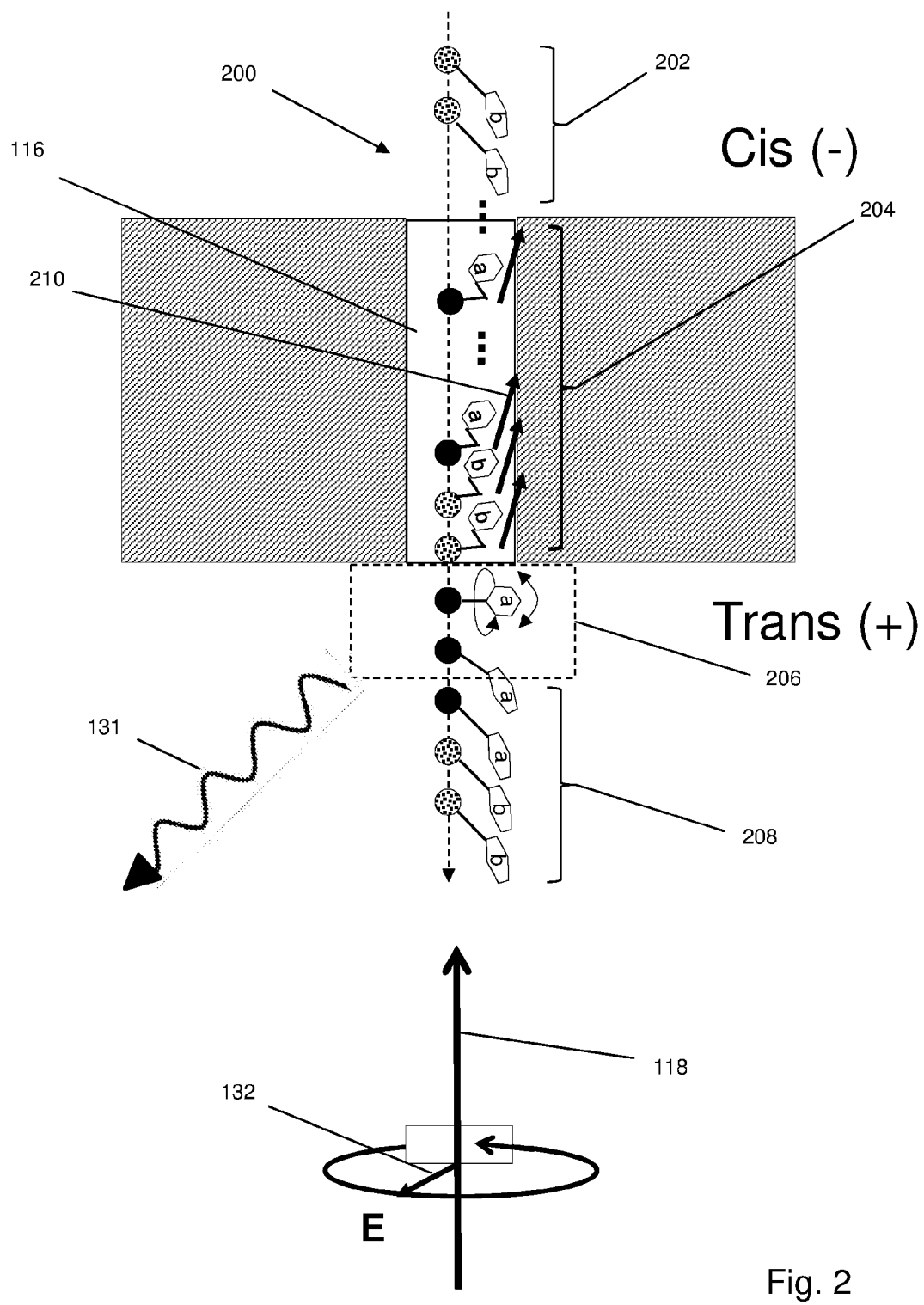
FIG. 2 illustrates an embodiment of the invention employing mutually and self-quenching fluorescent labels.

In some embodiments, fluorescent labels are selected so that they self-quench or mutually quench one another when attached to adjacent nucleotides of a polynucleotide in free solution; that is, in particular, the buffer solution used for translocating labeled polynucleotides through nanopores. Such self- or mutually quenching fluorescent labels reduce background signals and limit the time a fluorescent label is capable of being excited; or in other words, they limit the volume in which a fluorescent signal is generated to a region adjacent to exit (115) of nanopore (116). Use of self- and mutually quenching fluorescent labels is disclosed in U.S. patent publication 2016/0122812, which is incorporated herein by reference. Briefly, FIG. 2 illustrates the use of self- and mutually quenching fluorescent labels when two fluorescent labels having distinct signals are employed. Labeled single stranded polynucleotide (200) is shown translocating through nanopore (116). As in FIG. 1, different labels "a" and "b" are attached to two different kinds of nucleotide, again represented as filled circles and patterned circles. In this case, "a" and "b" are selected so that each self-quench when the same labels are on adjacent nucleotides in free solution or mutually quench when different labels are on adjacent nucleotides in free solution. Fluorescent labels of nucleotides (114) inside nanopore (116) are constrained so that absorption dipoles are oriented substantially orthogonally to the electrical vector of excitation beam (118), so that little or no excitation takes place. As nucleotides exit nanopore (116) their labels become mobile and amenable to excitation in region (206), prior to re-adopting a self- or mutually quenched configuration as polynucleotide (200) moves into the free solution of the Trans chamber.

Figure 3A:
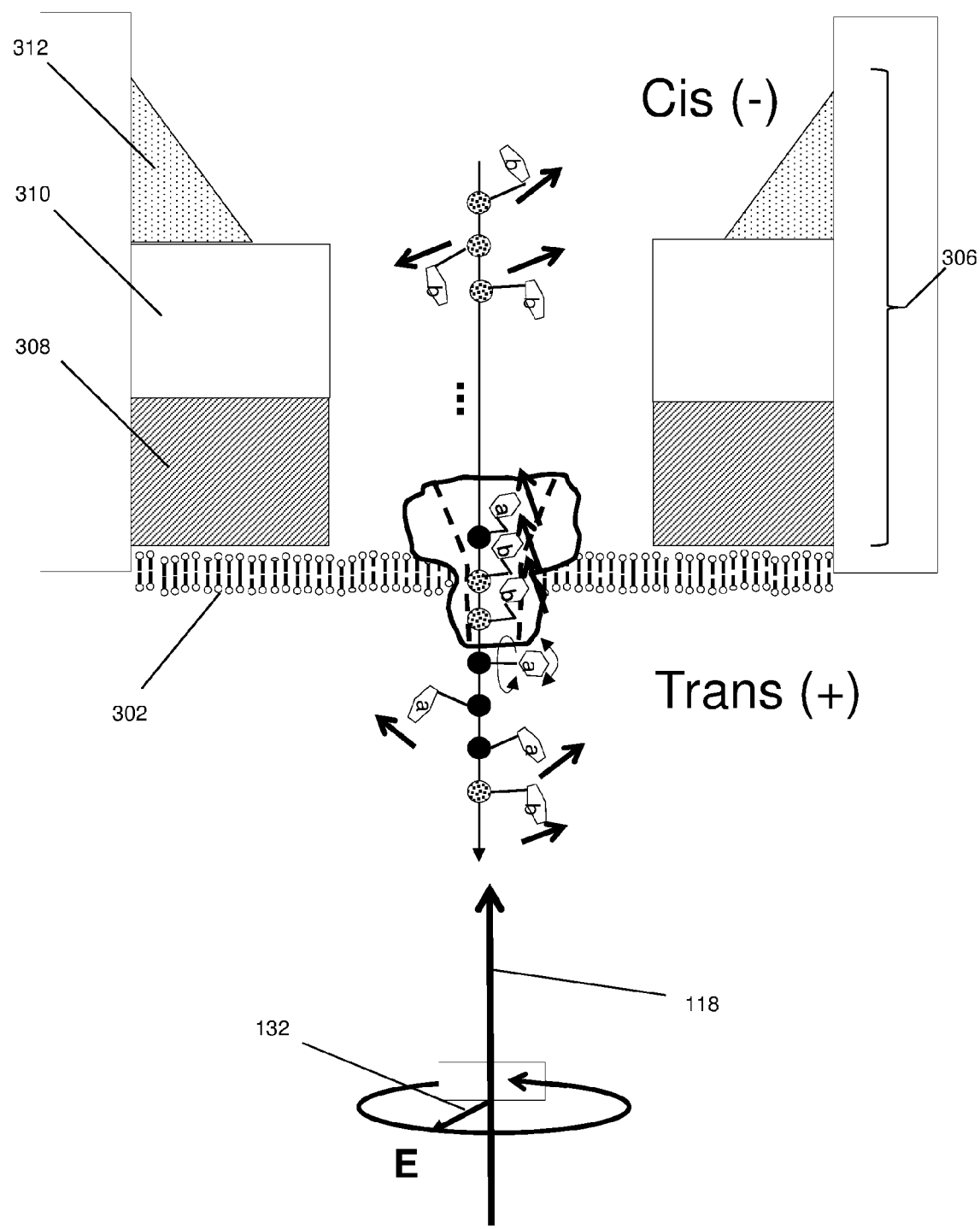
FIGS. 3A-3B illustrate embodiments of the invention using a protein nanopore and epi-illumination with a metal layer on the nanopore array to reduce background or TIR with FRET excitation.

As mentioned above, a wide variety of optical systems and nanopore configurations may be used with the invention. FIG. 3A illustrates components of one embodiment in which a protein nanopore (300) is disposed in a lipid bilayer (302) disposed (in turn) across aperture (304) of solid state membrane (306), which comprises opaque layer (308) (such as a metal layer), silicon nitride layer (310) and silicon support layer (312). Opaque layer (308) prevents or reduces transmission of excitation beam (314) through solid state membrane (306) where it could excite undesired background fluorescence. As polynucleotide (320) with differently labeled monomers (illustrated as filled circles (322) and patterned circles (324) as above) pass through nanopore (300), absorption dipoles (e.g. 305) are oriented to render them unresponsive to excitation beam (314).

Figure 3B:
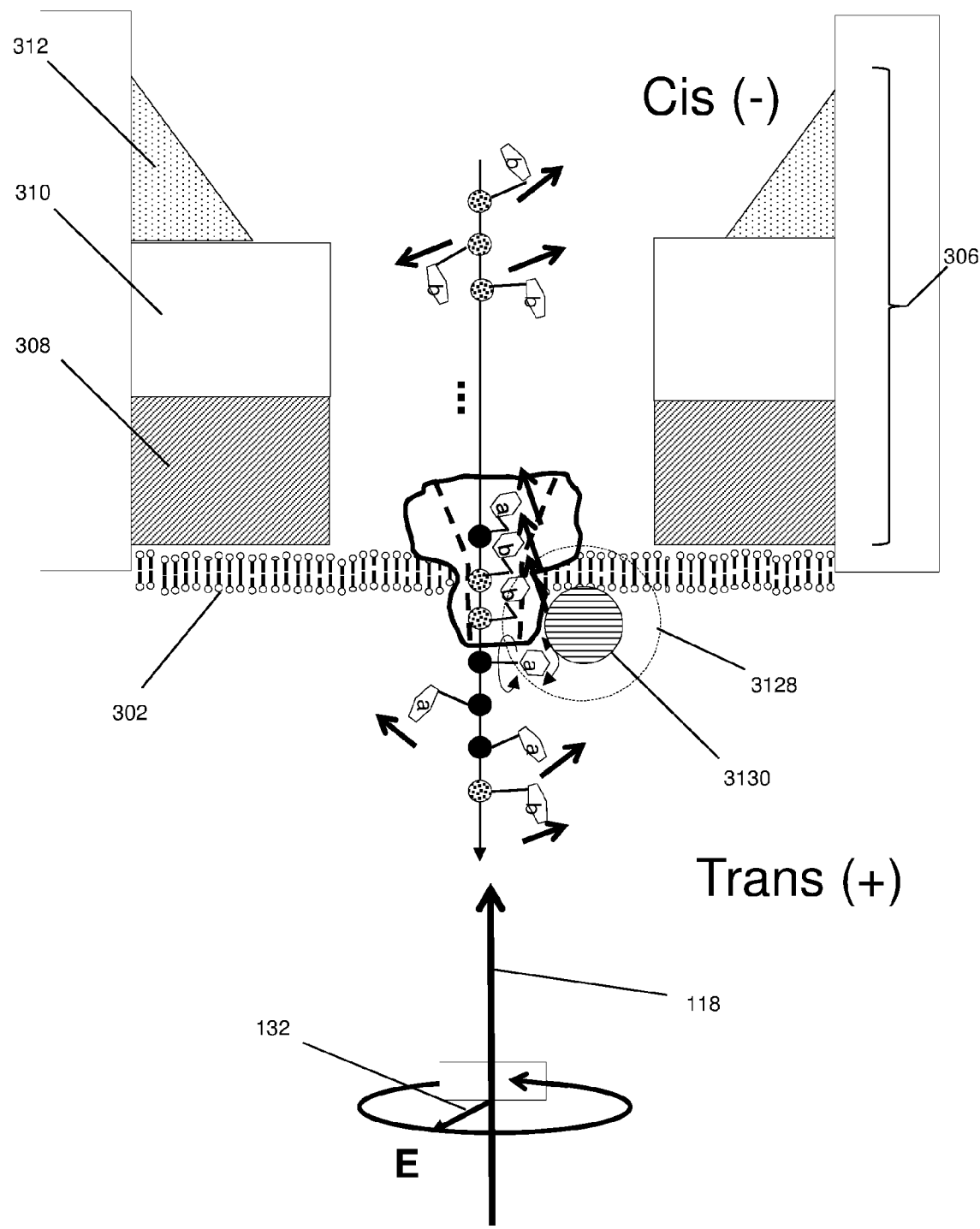

FIG. 3B illustrates a similar configuration as FIG. 3A with quantum dot (3130) attached to protein nanopore (300) adjacent to its Trans-side exit, so that whenever a fluorescent label emerges from the exit (and gains freedom of movement) it comes within a FRET distance (3128) of quantum dot (3130). Thus, upon exit the fluorescent label become capable of FRET excitation.

Embodiments Employing Mutually and Self-Quenching Labels

In some embodiments, self- and mutually quenching fluorescent labels may be used in addition to quenching agents in order to reduce fluorescent emissions outside of those from labels on nucleotides exiting nanopores. Use of such fluorescent labels is disclosed in U.S. patent publication 2016/0122812, which is incorporated by reference. In some embodiments, monomers are labeled with fluorescent labels that are capable of at least three states while attached to a target polynucleotide: (i) A substantially quenched state wherein fluorescence of an attached fluorescent label is quenched by a fluorescent label on an immediately adjacent monomer; for example, a fluorescent label attached to a polynucleotide in accordance with the invention is substantially quenched when the labeled polynucleotide is free in conventional aqueous solution for studying and manipulating the polynucleotide. (ii) A sterically constrained state wherein a labeled polynucleotide is translocating through a nanopore such that the free-solution movements or alignments of an attached fluorescent label is disrupted or limited so that there is little or no detectable fluorescent signal generated from the fluorescent label. (iii) A transition state wherein a fluorescent label attached to a polynucleotide transitions from the sterically constrained state to the quenched state as the fluorescent label exits the nanopore (during a "transition interval") while the polynucleotide translocates through the nanopore.

In part, this example is an application of the discovery that during the transition interval a fluorescent label (on an otherwise substantially fully labeled and self-quenched polynucleotide) is capable of generating a detectable fluorescent signal. Without the intention of being limited by any theory underlying this discovery, it is believed that the fluorescent signal generated during the transition interval is due to the presence of a freely rotatable dipole in the fluorescent label emerging from the nanopore, which renders the fluorescent label temporarily capable of generating a fluorescent signal, for example, after direct excitation or via FRET. In both the sterically constrained state as well as the quenched state, the dipoles are limited in their rotational freedom thereby reducing or limiting the number of emitted photons. In some embodiments, the polynucleotide is a polynucleotide, usually a single stranded polynucleotide, such as, DNA or RNA, but especially single stranded DNA. In some embodiments, the invention includes a method for determining a nucleotide sequence of a polynucleotide by recording signals generated by attached fluorescent labels as they exit a nanopore one at a time as a polynucleotide translocates through the nanopore. Upon exit, each attached fluorescent label transitions during a transition interval from a constrained state in the nanopore to a quenched state on the polynucleotide in free solution. In other words, in some embodiments, a step of the method of the invention comprises exciting each fluorescent label as it is transitioning from a constrained state in the nanopore to a quenched state on the polynucleotide in free solution. As mentioned above, during this transition interval or period the fluorescent label is capable of emitting a detectable fluorescent signal indicative of the nucleotide it is attached to.

In some embodiments, the invention includes an application of the discovery that fluorescent labels and nanopores may be selected so that during translocation of a polynucleotide through a nanopore fluorescent labels attached to monomers are forced into a constrained state in which they are incapable (or substantially incapable) of producing a detectable fluorescent signal. In some embodiments, nanopores are selected that have a bore, or lumen, with a diameter in the range of from 1 to 4 nm; in other embodiments, nanopores are selected that have a bore or lumen with a diameter in the range of from 2 to 3 nm. In some embodiments, such bore diameters are provided by a protein nanopore. In some embodiments, such nanopores are used to force fluorescent labels into a constrained state in accordance with the invention, so that whenever a fluorescent label exits a nanopore, it transitions from being substantially incapable of generating a fluorescent signal to being detectable and identifiable by a fluorescent signal it can be induced to emit. Thus, fluorescent labels attached to each of a sequence of monomers of a polynucleotide may be detected in sequence as they suddenly generate a fluorescent signal in a region immediately adjacent to a nanopore exit (a "transition zone" or "transition volume" or "detection zone"). In some embodiments, organic fluorescent dyes are used as fluorescent labels with nanopores of the above diameters. In some embodiments, at least one such organic fluorescent dye is selected from the set consisting of xanthene dyes, rhodamine dyes and cyanine dyes. Some embodiments for determining a monomer sequence of a polynucleotide may be carried out with the following steps: (a) translocating a polynucleotide through a nanopore, wherein monomers of the polynucleotide are labeled with fluorescent labels wherein the nanopore constrains fluorescent labels within its bore into a constrained state such that substantially no detectable fluorescent signal is generated therein; (b) directing to the nanopore an excitation beam having a predetermined polarization state to excite the fluorescent label of each monomer upon its exit from the nanopore; (c) measuring a fluorescent signal in a detection zone generated by the exiting fluorescent label to identify the monomer to which the fluorescent label is attached; (d) quenching fluorescent signals from excited fluorescent labels outside of the detection zone, and (d) determining a monomer sequence of the polynucleotide from a sequence of fluorescent signals. In further embodiments, fluorescent labels are acceptors of a FRET pair and one or more donors of the FRET pair are attached to the nanopore within a FRET distance of the exit.

In some embodiments, "substantially quenched" as used above means a fluorescent label generates a fluorescent signal at least thirty percent reduced from a signal generated under the same conditions, but without adjacent mutually quenching labels. In some embodiments, "substantially quenched" as used above means a fluorescent label generates a fluorescent signal at least fifty percent reduced from a signal generated under the same conditions, but without adjacent mutually quenching labels.

In some embodiments, a nucleotide sequence of a target polynucleotide is determined by carrying out four separate reactions in which copies of the target polynucleotide have each of its four different kinds of nucleotide (A, C, G and T) labeled with a single fluorescent label. In a variant of such embodiments, a nucleotide sequence of a target polynucleotide is determined by carrying out four separate reactions in which copies of the target polynucleotide have each of its four different kinds of nucleotide (A, C, G and T) labeled with one fluorescent label while at the same time the other nucleotides on the same target polynucleotide are labeled with a second fluorescent label. For example, if a first fluorescent label is attached to A's of the target polynucleotide in a first reaction, then a second fluorescent label is attached to C's, G's and T's (i.e. to the "not-A" nucleotides) of the target polynucleotides in the first reaction. Likewise, in continuance of the example, in a second reaction, the first label is attached to C's of the target polynucleotide and the second fluorescent label is attached to A's, G's and T's (i.e. to the "not-C" nucleotides) of the target polynucleotide. And so on, for nucleotides G and T.

The same labeling scheme may be expressed in terms of conventional terminology for subsets of nucleotide types; thus, in the above example, in a first reaction, a first fluorescent label is attached to A's and a second fluorescent label is attached to B's; in a second reaction, a first fluorescent label is attached to C's and a second fluorescent label is attached to D's; in a third reaction, a first fluorescent label is attached to G's and a second fluorescent label is attached to H's; and in a fourth reaction, a first fluorescent label is attached to T's and a second fluorescent label is attached to V's.

In some embodiments, a polymer, such as a polynucleotide or peptide, may be labeled with a single fluorescent label attached to a single kind of monomer, for example, every T (or substantially every T) of a polynucleotide is labeled with a fluorescent label, e.g. a cyanine dye. In such embodiments, a collection, or sequence, of fluorescent signals from the polynucleotide may form a signature or fingerprint for the particular polynucleotide. In some such embodiments, such fingerprints may or may not provide enough information for a sequence of monomers to be determined.

In some embodiments, a feature of the invention is the labeling of substantially all monomers of a polynucleotide analyte with fluorescent dyes or labels that are members of a mutually quenching set. The use of the term "substantially all" in reference to labeling polynucleotide analytes is to acknowledge that chemical and enzymatic labeling techniques are typically less than 100 percent efficient. In some embodiments, "substantially all" means at least 80 percent of all monomer have fluorescent labels attached. In other embodiments, "substantially all" means at least 90 percent of all monomer have fluorescent labels attached. In other embodiments, "substantially all" means at least 95 percent of all monomer have fluorescent labels attached. Mutually quenching sets of fluorescent dyes have the following properties: (i) each member quenches fluorescence of every member (for example, by FRET or by static or contact mechanisms), and (ii) each member generates a distinct fluorescent signal when excited and when in a non-quenched state. That is, if a mutually quenching set consists of two dyes, D1 and D2, then (i) D1 is self-quenched (e.g. by contact quenching with another D1 molecule) and it is quenched by D2 (e.g. by contact quenching) and (ii) D2 is self-quenched (e.g. by contact quenching with another D2 molecule) and it is quenched by D1 (e.g. by contact quenching). Guidance for selecting fluorescent dyes or labels for mutually quenching sets may be found in the following references, which are incorporated herein by reference: Johansson, Methods in Molecular Biology, 335: 17-29 (2006); Marras et al, Nucleic Acids Research, 30: e122 (2002); and the like. In some embodiments, members of a mutually quenching set comprise organic fluorescent dyes that components or moieties capable of stacking interactions, such as aromatic ring structures. Exemplary mutually quenching sets of fluorescent dyes, or labels, may be selected from rhodamine dyes, fluorescein dyes and cyanine dyes. In one embodiment, a mutually quenching set may comprise the rhodamine dye, TAMRA, and the fluorescein dye, FAM. In another embodiment, mutually quenching sets of fluorescent dyes may be formed by selecting two or more dyes from the group consisting of OREGON GREEN 488, Fluorescein-EX, fluorescein isothiocyanate, Rhodamine Red-X, Lissamine rhodamine B, Calcein, Fluorescein, Rhodamine, one or more BODIPY dyes, TEXAS RED dye, OREGON GREEN 514 dye, and one or more ALEXA FLUOR dyes. Representative BODIPY dyes include BODIPY FL, BODIPY R6G, BODIPY TMR, BODIPY 581/591, BODIPY TR, BODIPY 630/650 and BODIPY 650/665. Representative ALEXA FLUOR dyes include ALEXA FLUORS 350, 405, 430, 488, 500, 514, 532, 546, 555, 568, 594, 610, 633, 635, 647, 660, 680, 700, 750 and 790.

As above, in some embodiments, a monomer sequence of a target polynucleotide is determined by carrying out separate reactions (one for each kind of monomer) in which copies of the target polynucleotide have each different kind of monomer labeled with a mutually- or self-quenching fluorescent label. In other embodiments, a monomer sequence of a target polynucleotide is determined by carrying out separate reactions (one for each kind of monomer) in which copies of the target polynucleotide have each different kind of monomer labeled with a different mutually quenching fluorescent label selected from the same mutually quenching set. In embodiments in which a mutually quenching set contains only two dyes, then a selected monomer (say, monomer X) is labeled with a first mutually quenching dye and every other kind of monomer (i.e., not-monomer X) is labeled with a second mutually quenching dye from the same set. Thus, steps of the embodiment generate a sequence of two different fluorescent signals, one indicating monomer X and another indicating not-monomer X.

In some embodiments, a single fluorescent label (for example, attached to a single kind of monomer in a polynucleotide comprising multiple kinds of monomers) may be used that is self-quenching when attached to adjacent monomers (of the same kind) on a polynucleotide, such as adjacent nucleotides of a polynucleotide. Exemplary self-quenching fluorescent labels include, but are not limited to, OREGON GREEN 488, fluorescein-EX, FITC, Rhodamine Red-X, Lissamine rhodamine B, calcein, fluorescein, rhodamine, BODIPY dyes, and TEXAS RED dye, e.g. which are disclosed in Molecular Probes Handbook, 11th Edition (2010).

Embodiments Employing Quenching Agents

Figure 3C:
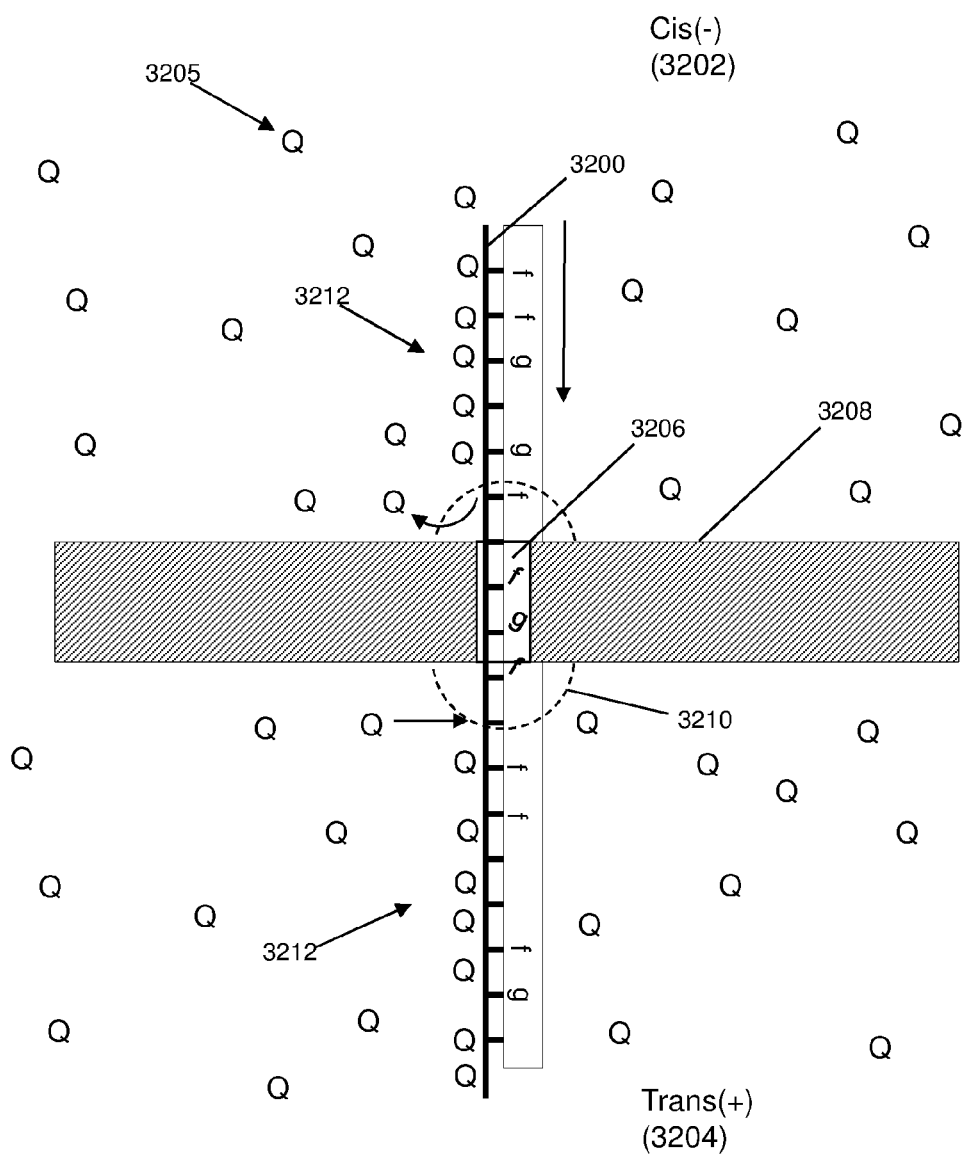
FIGS. 3C-3D illustrate embodiments employing quenching agents.

In some embodiments of the invention quenching agents may be applied in a nanopore device to prevent undesired fluorescence. For example, quenching agents may be present in the trans chamber only, the cis chamber only, or both cis and trans chambers (FIG. 3C). In FIG. 3C, labeled polynucleotide (3200) is illustrated translocating nanopore (3206) of solid phase membrane (3208) from cis chamber (3202) to trans chamber (3204) Immersed in trans chamber (3204) are non-fluorescent quenching agents (3205) designated by "Q". Quenching agents of the invention are soluble under translocation conditions for labeled polynucleotide (3200), and under the same conditions, quenching agents bind to single stranded polynucleotides, such as (3200), without substantial sequence specificity. As explained more fully below, a large variety of non-fluorescent quenching agents are available for use with the invention, which include derivatives of many well-known organic dyes, such as asymmetric cyanine dyes, as well as conjugates of such compounds and oligonucleotides and/or analogs thereof. In this embodiment, selection of the type and concentration of quenching agent and the translocation speed define detection zone (3210). In some embodiments, "detection zone" means a region or volume (which may be contiguous or non-contiguous) from which fluorescent signals are collected to form the raw data from which information, such as sequence information, about a labeled polynucleotide is determined. Fluorescent labels in trans chamber (3204) outside of detection zone (3210) are substantially quenched by quenching agents (3205) bound to the portion of labeled polynucleotide (3200) in trans chamber (3204). In some embodiments, quenching agents comprise an oligonucleotide or analog conjugated to one or more quenching moieties based on organic dyes as described more fully below. Embodiments with quenching agents only in a trans chamber may be employed when, for example, solid phase membrane (3208) is or comprises an opaque layer so that fluorescent labels in cis chamber (3202) are substantially non-excited.

Figure 3D:
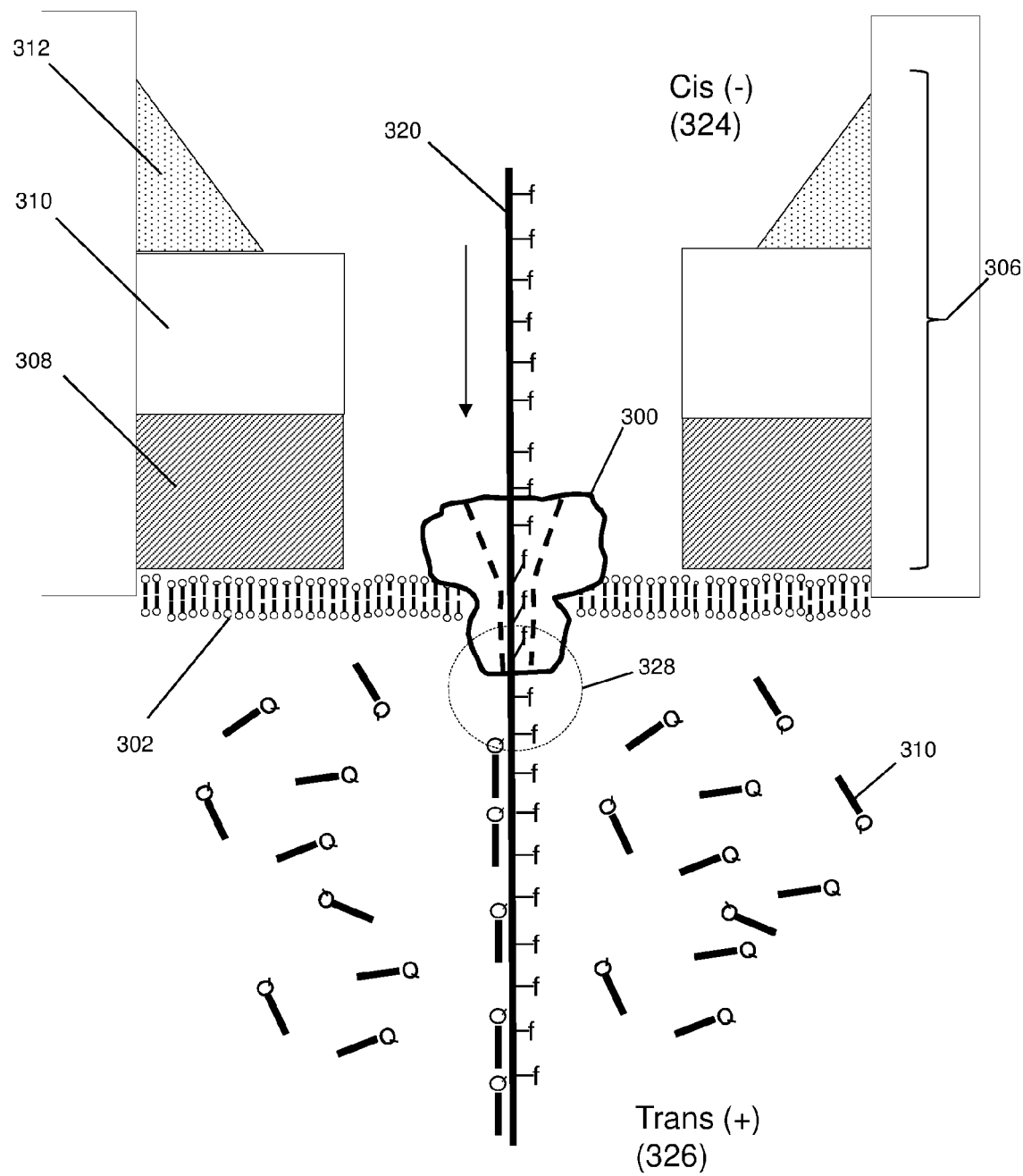

FIG. 3D illustrates an embodiment which includes the following elements: protein nanopore (300) disposed in lipid bilayer (302); epi-illumination of fluorescent labels with opaque layer (308) in solid phase membrane (306) to prevent or reduce background fluorescence; and quenching agents (310) disposed in trans chamber (326). As above, polynucleotide (320) with fluorescently labeled nucleotides (labels being indicated by "f", as with (322)) is translocated through nanopore (300) from cis chamber (324) to trans chamber (326). Oligonucleotide quenchers (310) are disposed in trans chamber (326) under conditions (e.g. concentration, temperature, salt concentration, and the like) that permits hybridization of oligonucleotide quenchers (328) to portions of polynucleotide (320) emerging from nanopore (300). Nanopore (300) may be selected so that signals from fluorescent labels are suppressed during transit of the nanopore as described in Huber et al, U.S. patent publication US 2016/0076091, which is incorporated herein by reference. Thus, when labeled nucleotides emerge from nanopore (300) in region (328) they become unsuppressed and capable of generating a signal. With most if not all forms of direct illumination (e.g. non-FRET) such emerged labels would continue to emit fluorescence as they travel further into trans chamber (326), thereby contributing greatly to a collected signal. With quenching agents in trans chamber (326) that bind to the emerging polynucleotide, such emissions can be significantly reduced and can define detection zone (328) from which collected signals can be analyzed to give nucleotide sequence information about polynucleotide (320). In some embodiments, a fluorescent signal from a single fluorescent label is detected from detection zone (328) during a detection period as the labeled polynucleotide moves through the detection zone. In other embodiments, a plurality of fluorescent signals is collected from a plurality of fluorescent labels in detection zone (328) during a predetermined time period. In some embodiments, such detection period is less than 1 msec, or less than 0.1 msec, or less than 0.01 msec. In some embodiments, such detection period is at least 0.01 msec, or at least 0.1 msec, or at least 0.5 msec.

Quenching agents of the invention comprise any compound (or set of compounds) that under nanopore sequencing conditions is (i) substantially non-fluorescent, (ii) binds to single stranded nucleic acids, particularly single stranded DNA, and (iii) absorbs excitation energy from other molecules non-radiatively and releases it non-radiatively. In some embodiments, quenching agents further bind non-covalently to single stranded DNA. A large variety of quenching compounds are available for use with the invention including, but not limited to, non-fluorescent derivatives of common synthetic dyes such as cyanine and xanthene dyes, as described more fully below. Guidance in selecting quenching compounds may be found in U.S. Pat. Nos. 6,323,337; 6,750,024 and like references, which are incorporated herein by reference.

In some embodiments, a quenching agent may be a single stranded DNA binding dye that has been covalently modified with a heavy atom that is known to quench fluorescence (such as bromine or iodine), or covalently modified with other groups known to quench fluorescence, such as a nitro group or an azo group. An example of dye that is known to bind single stranded DNA is SYBR GREEN dye (Zipper et al, (2004), Nucleic Acids Research. 32 (12)). Incorporation of a nitro, bromine, iodine, and/or azo groups into the cyanine SYBR GREEN structure provides a single stranded DNA binding group moiety that will quench fluorescent labels that might be present on a DNA.

In some embodiments, quenching agents comprise a binding moiety and one or more quenching moieties. Binding moieties may include any compound that binds to single stranded nucleic acids without substantial sequence specificity. Binding moieties may comprise peptides or oligonucleotides or analogs of either having modified linkages and/or monomers. Oligonucleotides and their analogs may provide binding to polynucleotides via duplex formation or via non-base paired aptameric binding. In some embodiments, binding moieties comprise an oligonucleotide or analog thereof having a length in the range of from 6 to 60 nucleotides. Such oligonucleotides or analogs may be conjugated to one quenching moiety or to a plurality of quenching moieties. In some embodiments, the plurality of quenching moieties conjugated to each oligonucleotide or analog is 2 or 3. Quenching moieties conjugated to a binding moiety may be the same or different. In some embodiments, whenever a binding moiety is an oligonucleotide or analog, two quenching moieties are conjugated thereto, one at a 5' end and one at a 3' end of the oligonucleotide. Oligonucleotides or analogs having from 2 to 3 quenching moieties may be synthesized using conventional linkage and synthetic chemistries, for example, as disclosed in the references cited herein.

Oligonucleotides or analogs may be provided as a single species or they may be provided as mixtures of a plurality of oligonucleotides or analogs with different sequences, and therefore, different binding specificities. In some embodiments, oligonucleotides or analogs are random sequence polymers; that is, they are provided as mixtures of every possible sequence of a given length. For example, such oligonucleotides or analogs may be represented by the formulas, "NNNNNN" for 6-mers, or "NNNNNNNN" for 8-mers, wherein N may be A, C, G or T, or an analog thereof.

"Analogs" in reference to oligonucleotides means an oligonucleotide that contains one or more nucleotide analogs. As described in the definition section, a "nucleotide analog" is a nucleotide that may have a modified linkage moiety, sugar moiety or base moiety. Exemplary oligonucleotide analogs that may be used with the invention include, but are not limited to, peptide nucleic acids (PNAs), locked nucleic acids (LNAs)(2'-O-methyl RNA), phosphorothioate oligonucleotides, bridged nucleic acids (BNAs), or the like.

In some embodiments, oligonucleotide binding moieties comprise universal bases; that is, they contain one or more nucleotide analogs that can replace any of the four natural nucleotides without destabilizing base-pair interactions. Nucleotide analogs having universal base properties are described in Loakes, Nucleic Acids Research, 29(12): 2437-2447 (2001), which is incorporated herein by reference. In some embodiments, oligonucleotide binding moieties comprise 2'-deoxyinosine, 7-deaza-2'-deoxyinosine, 2-aza-2'-deoxyinosine, 3-nitropyrrole nucleotides, 5-nitroindole nucleotides, or the like.

In some embodiments, quenching agents may comprise a combination of two or more compounds that act together to quench undesired fluorescent signals of a single stranded labeled polynucleotide. For example, a quenching agent may comprise an oligonucleotide (e.g., polydeoxyinosine) that may form a duplex with the labeled polynucleotide and separately a double stranded intercalator that is a quencher. Thus, whenever the polydeoxyinosine binds to a labeled polynucleotide, the quenching intercalator binds to the resulting duplex and quenches fluorescent signals from the polynucleotide.

Any synthetic dye that can detectably quench fluorescent signals of the fluorescent labels of a labeled polynucleotide is an acceptable quenching moiety for the purposes of the invention. Specifically, as used in the invention, the quenching moieties possess an absorption band that exhibits at least some spectral overlap with an emission band of the fluorescent labels on a labeled polynucleotide. This overlap may occur with emission of the fluorescent label (donor) occurring at a lower or even higher wavelength emission maximum than the maximal absorbance wavelength of the quenching moiety (acceptor), provided that sufficient spectral overlap exists. Energy transfer may also occur through transfer of emission of the donor to higher electronic states of the acceptor. One of ordinary skill in the art determines the utility of a given quenching moiety by examination of that dye's excitation bands with respect to the emission spectrum of the fluorescent labels being used.

Typically, fluorescence quenching in the invention occurs through Fluorescence Resonance Energy Transfer (FRET or through the formation of charge transfer complexes) between a fluorescent label and a quenching moiety of the invention. The spectral and electronic properties of the donor and acceptor compounds have a strong effect on the degree of energy transfer observed, as does the separation distance between the fluorescent labels on the labeled polynucleotide and the quenching moiety. As the separation distance increases, the degree of fluorescence quenching decreases.

A quenching moiety may be optionally fluorescent, provided that the maximal emission wavelength of the dye is well separated from the maximal emission wavelength of the fluorescent labels when bound to labeled polynucleotides. Preferably, however, the quenching moiety is only dimly fluorescent, or is substantially non-fluorescent, when covalently conjugated to a oligonucleotide or analog. Substantially non-fluorescent, as used herein, indicates that the fluorescence efficiency of the quenching moiety in an assay solution as described for any of the methods herein is less than or equal to 5 percent, preferably less than or equal to 1 percent. In other embodiments, the covalently bound quenching moiety exhibits a quantum yield of less than about 0.1, more preferably less than about 0.01. In some embodiments, the fluorescence of fluorescent labels associated with a quenching oligonucleotide of the invention is quenched more than 50% relative to the same oligonucleotide associated with the same fluorescent labels in the absence of the covalently bound quenching moiety. In another embodiment, the fluorescent labels are quenched more than 90% relative to the unlabeled oligonucleotide. In yet another embodiment, the nucleic acid stains are quenched more than 95% relative to the unlabeled oligonucleotide.

In some embodiments, a quenching moiety may be a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a carbocyanine, a carbostyryl, a porphyrin, a salicylate, an anthranilate, an azulene, a perylene, a pyridine, a quinoline, a coumarin (including hydroxycoumarins and aminocoumarins and fluorinated and sulfonated derivatives thereof (as described in U.S. Pat. No. 5,830,912 to Gee et al. (1998) and U.S. Pat. No. 5,696,157 to Wang et al. (1997), incorporated by reference), a polyazaindacene (e.g. U.S. Pat. No. 4,774,339 to Haugland, et al. (1988); U.S. Pat. No. 5,187,288 to Kang, et al. (1993); U.S. Pat. No. 5,248,782 to Haugland, et al. (1993); U.S. Pat. No. 5,274,113 to Kang, et al. (1993); U.S. Pat. No. 5,433,896 to Kang, et al. (1995); U.S. Pat. No. 6,005,113 to Wu et al. (1999), all incorporated by reference), a xanthene, an oxazine or a benzoxazine, a carbazine (U.S. Pat. No. 4,810,636 to Corey (1989), incorporated by reference), or a phenalenone or benzphenalenone (U.S. Pat. No. 4,812,409 Babb et al. (1989), incorporated by reference).

In other embodiments, quenching moieties that are substantially non-fluorescent dyes include in particular azo dyes (such as DABCYL or DABSYL dyes and their structural analogs), triarylmethane dyes such as malachite green or phenol red, 4',5z-diether substituted fluoresceins (U.S. Pat. No. 4,318,846 (1982)), or asymmetric cyanine dye quenchers (PCT Int. App. WO 99 37,717 (1999)).

In embodiments where the quenching moiety is a xanthene, the synthetic dye is optionally a fluorescein, a rhodol (U.S. Pat. No. 5,227,487 to Haugland, et al. (1993), incorporated by reference), or a rhodamine. As used herein, fluorescein includes benzo- or dibenzofluoresceins, seminaphthofluoresceins, or naphthofluoresceins. Similarly, as used herein rhodol includes seminaphthorhodafluors (U.S. Pat. No. 4,945,171 to Haugland, et al. (1990), incorporated by reference). Xanthenes include fluorinated derivatives of xanthene dyes (Int. Publ. No. WO 97/39064, Molecular Probes, Inc. (1997), incorporated by reference), and sulfonated derivatives of xanthene dyes (Int. Publ. No. WO 99/15517, Molecular Probes, Inc. (1999), incorporated by reference). As used herein, oxazines include resorufms, aminooxazinones, diaminooxazines, and their benzo-substituted analogs.

In further embodiments, the quenching moiety is an substantially nonfluorescent derivative of 3- and/or 6-amino xanthene that is substituted at one or more amino nitrogen atoms by an aromatic or heteroaromatic ring system, e.g. as described in U.S. Pat. No. 6,399,392, which is incorporated herein by reference. These quenching dyes typically have absorption maxima above 530 nm, have little or no observable fluorescence and efficiently quench a broad spectrum of luminescent emission, such as is emitted by chemiluminphores, phosphors, or fluorophores. In one embodiment, the quenching dye is a substituted rhodamine. In another embodiment, the quenching compound is a substituted rhodol.

In still other embodiments, a quenching moiety may comprise one or more non-fluorescent quenchers known as BLACK HOLE QUENCHER™ compounds (BHQs) described in the following patents, which are incorporated herein by reference: U.S. Pat. Nos. 7,019,129; 7,109,312; 7,582,432; 8,410,025; 8,440,399; 8,633,307; 8,946,404; 9,018,369; or 9,139,610.

Additional quenching moieties are disclosed in the following, which are incorporated herein by reference: U.S. Pat. Nos. 6,699,975; 6,790,945; and 8,114,979.

Optical Signal Detection

Figure 4:
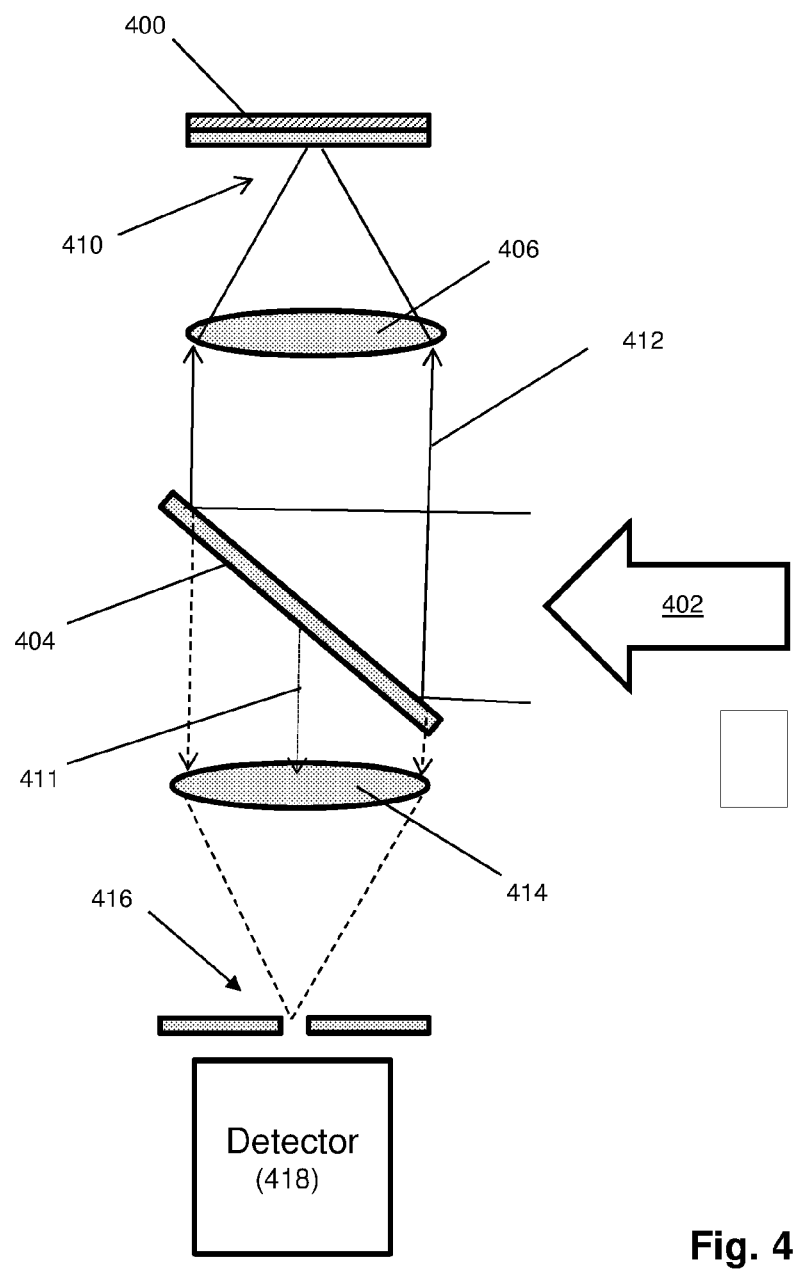
FIG. 4 illustrates the basic components of a confocal epi-illumination system.

In some embodiments, an epi-illumination system, in which excitation beam delivery and optical signal collection occurs through a single objective, may be used for direct illumination of labels on a polymer analyte or donors on nanopores. The basic components of a confocal epi-illumination system for use with the invention is illustrated in FIG. 4. Excitation beam (402) is directed to dichroic (404) and onto (412) objective lens (406) which focuses (410) excitation beam (402) onto layered membrane (400), in which labels are excited directly to emit an optical signal, such as a fluorescent signal, or are excited indirectly via a FRET interaction to emit an optical signal. Such optical signal is collected by objective lens (406) and directed to dichroic (404), which is selected so that it passes light of optical signal (411) but reflects light of excitation beam (402). Optical signal (411) passes through lens (414) which focuses it through pinhole (416) and onto detector (418).

Figure 5:
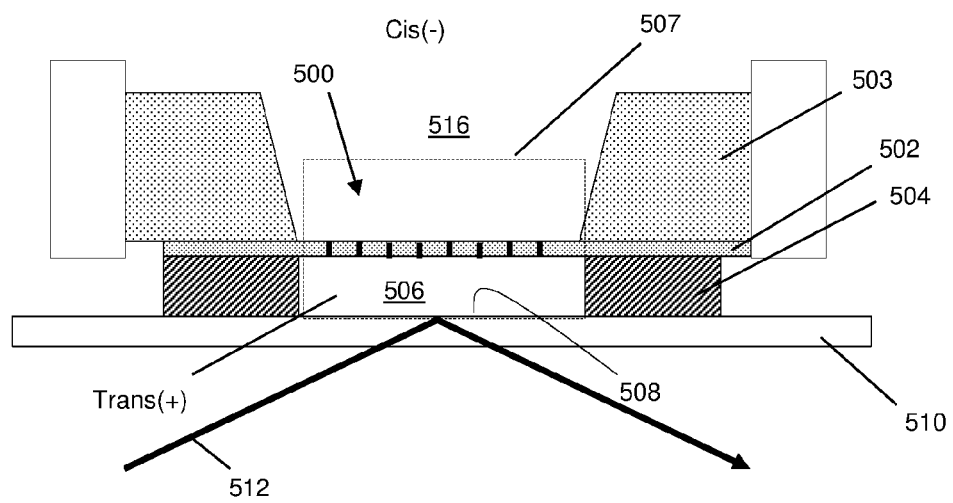
FIG. 5 illustrates elements of a TIRF system for excitation of optical labels in or near a nanopore array without FRET signal generation.

In some embodiments, labels on monomers may be excited by an evanescence field using an apparatus similar to that shown in FIG. 5, described in Soni et al, Review of Scientific Instruments, 81: 014301 (2010); and in U.S. patent publication 2012/0135410, which is incorporated herein by reference. In this apparatus, a very narrow second chamber on the trans side of a nanopore or nanopore array permits an evanescent field to extend from a surface of an underlying glass slide to establish excitation zones both at entrances and exits of the nanopores, so that each optical measurement associated with a nanopore contains contributions from a plurality of labeled monomers. Array of apertures (500) (which may include protein nanopores inserted in a lipid bilayer), may be formed in silicon nitride layer (502), which may have a thickness in the range of from 20-100 nm. Silicon nitride layer (502) may be formed on a silicon support layer (503). Second chamber (506) may be formed by silicon nitride layer (502), silicon dioxide layer (504) which determines the height of second chamber (506), and surface (508) of glass slide (510). Silicon dioxide layer (504) may have a thickness in the range of from 50-100 nm. A desired evanescent field (507) extending from surface (508) across silicon nitride layer (502) may be established by directing light beam (512) at an appropriate angle relative to glass slide (510) so that TIR occurs. For driving labeled polynucleotide analytes through array (500), cis(−) conditions may be established in first chamber (516) and trans(+) conditions may be established in second chamber (506) with electrodes operationally connected to first and second chambers (506 and 521).

Sequence Determination with Mixed Optical Signals

In some embodiments, a series of optical signals may be measured from a resolution limited area wherein each optical measurement comprises a plurality of component signals from different adjacent monomers (whose order in the polymer cannot be determined from a single measurement because, for example, the component signals are generated from within a diffraction limited area). Under these circumstances, optically-based nanopore analysis of polymers (i) generates a time series of optical measurements that comprise overlapping contributions from sequences of more than one labeled monomer, thereby making it difficult, if not impossible, to determine an ordering of the monomers from a single measurement, and (ii) by selecting optical labels for monomers which generate distinguishable signals, the optical measurements can be separated into contributions from different labels on different kinds of monomers, which allows overlapping measurements to be converted into sequence information.

In one aspect, a method of the invention may be implemented by the following steps: (a) translocating a polymer through a nanopore, wherein different kinds of monomers of the polymer are labeled with different optical labels that generate distinguishable optical signals and wherein the nanopore constrains the monomers to move single file through an excitation zone that encompasses a plurality of monomers; (b) detecting a time series of optical signals from the monomers as the polymer passes through the excitation zone; (c) separating optical signals from different kinds of monomers; and (d) determining a sequence of monomers from time series of separated optical signals from the polymer.

In accordance with the invention, when a labeled polymer translocates through a nanopore and its associated excitation zones, a time-ordered set of optical measurements are recorded. Optical measurements at adjacent time points are overlapping in the sense that each optical measurement contains contributions from labels of adjacent monomers. Thus, for example, if three monomers generate signals at each time point (for example, B, C and D of polymer . . . -A-(B-C-D)- . . . moving through an excitation zone from left to right), and if one monomer exits the excitation zone and another monomer enters the excitation zone (indicated by parentheses) between successive measurements (for example, A enters and D exits: -(A-B-C)-D . . . ), then two successive optical measurements will contain contributions from the same monomers (in this example, both measurements include contributions from B and C. The above example is based on a very simplified model of polymer translocation through nanopores; however, the concept of successive overlapping optical measurements is applicable to more complex descriptions of polymer translocation.

Since emissions from a plurality of different labeled monomers at a nanopore originate from the same resolution limited area, relative position information (in particular, sequence information) about the monomers cannot be determined from a single optical measurement. However, because of the overlap and the use of labels that generate monomer-specific signals, in some embodiments, sequence information may be determined from the time-ordered set of optical signal measurements when it is separated into a plurality of time-ordered sets of monomer-specific signals. Algorithms similar to those used in sequencing-by-hybridization (SBH) to reconstruct target polynucleotide sequences from hybridization data may be used to reconstruct target polynucleotides here, e.g. U.S. Pat. No. 5,002,867; Timp et al, Biophys. J., 102: L37-L39 (2012); or the like, which are incorporated by reference. The constraints of (i) time-ordered overlapping signals and signals and (ii) their separation into monomer-specific components significantly simplify the determination step in the case of optical detection.

Figure 6:
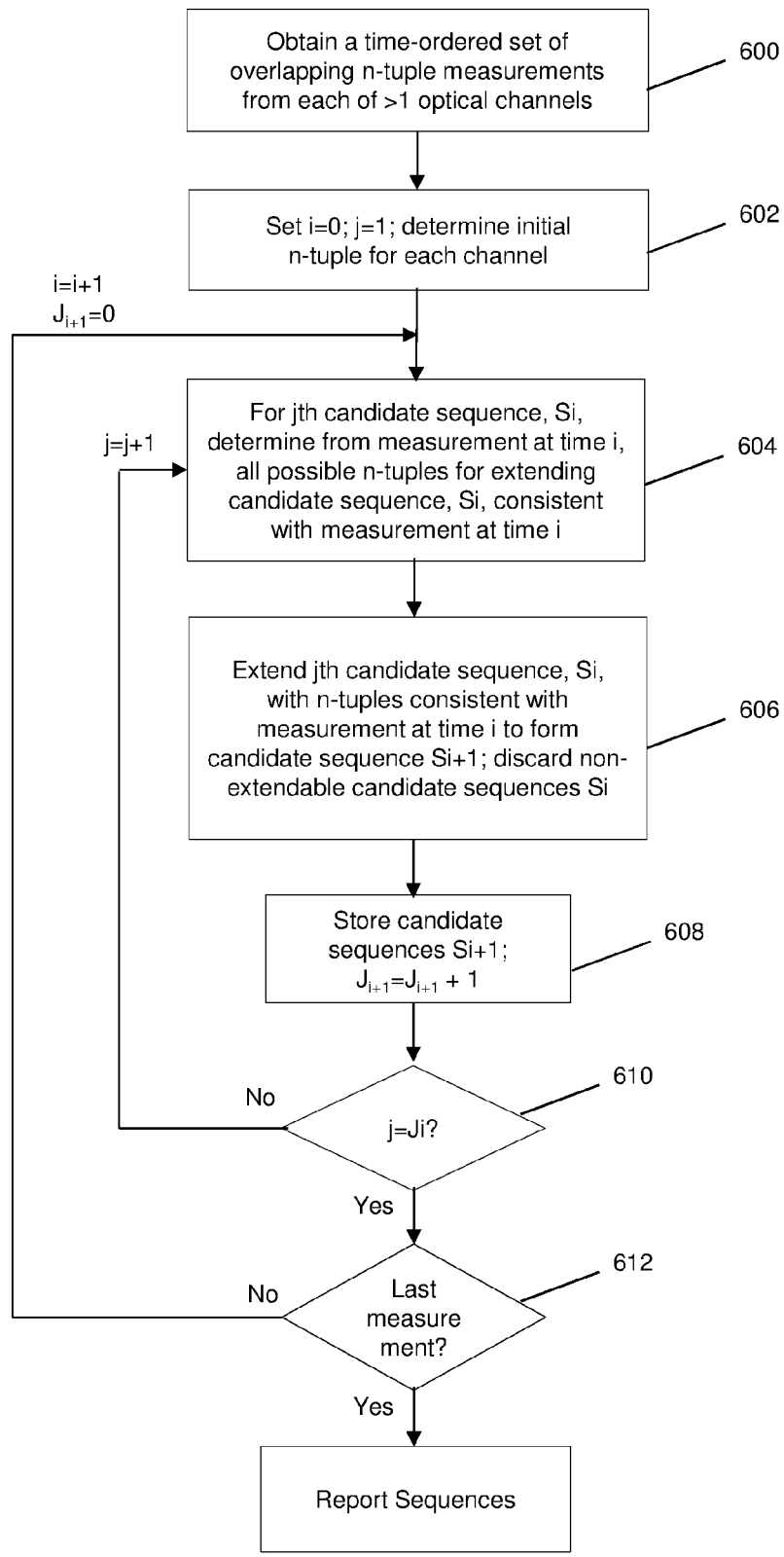
FIG. 6 is a flow chart illustrating a step for calling nucleotide sequences based on measurements of optical signals comprising light from multiple optical labels.

FIG. 6 illustrates one embodiment of a step for determining monomer sequence information from a time-ordered set of overlapping optical signals based on a simple model of nanopore translocation. The simple model assumes that optical measurements at each time step (except at the entry and exit of a polymer from a nanopore) each contain signal contributions from the same number of monomers (referred to in FIG. 6 as an "n-tuple" to indicate that a measurement would contain contributions from n monomers). It is understood that more complex models may allow for differing numbers of contributing monomers in each measurement, for local variations in translocation speed, deviations in linear movement of monomers, and other like phenomena. That is, in some embodiments, optical measurements at different times may have contributions from different numbers of nucleotides. In some embodiments, the differing number of nucleotides are ordered along a segment of the target polynucleotide. The step of determining illustrated by FIG. 6 assumes that a labeled polymer has passed through a nanopore and that a time ordered set of optical measurements has been made, including separation of optical signals into monomer-specific signals (600). The entry and exit of a polymer are treated differently since there are necessarily different numbers of monomers in the excitation zone(s) upon entry and exit. In this embodiment, it is assumed that initial and final optical measurements under these conditions permits the initial and final monomers to be determined directly from their monomer-specific signal. In other embodiments, preparation of labeled polymers for analysis may include insertion of a plurality of predetermined labeled nucleotides at one or both ends of such labeled polymers for the purpose of generating a known sequence of optical signals to aid in a sequence determination step. Such predetermined labeled nucleotides would be similar to key sequences in Ion Torrent or 454 sequencing, e.g. U.S. Pat. No. 7,575,865, which is incorporated by reference.

Returning to FIG. 6, at the beginning of a determining step, time index, i, is set to zero; the index, j, for candidate sequences at the current time, i, is set to 1 (602); and the initial n-tuple of the set of monomer-specific time-ordered optical signals is examined (604). Such examination comprises first determining from the measurement at time i all possible n-tuples of monomers that are consistent with the measurement, then determining from those n-tuples which ones that properly overlap candidate sequence Si. New candidate sequences Si+1 are formed (and a sequence Si is extended) by each properly overlapping n-tuple for the set consistent with the measurement (606). New extended candidate sequences, Si+1, are stored and the index giving the number of candidate sequences at time i+1, Ji+1, is updated (608). This step is repeated until every candidate sequence, Si, has been examined (610), and a similar examination is carried out at each time, i, until each optical measurement in the time-ordered set has been examined.

Nanopores and Nanopore Arrays

Nanopores used with the invention may be solid-state nanopores, protein nanopores, or hybrid nanopores comprising protein nanopores or organic nanotubes such as carbon or graphene nanotubes, configured in a solid-state membrane, or like framework. Important features of nanopores include constraining polymer analytes, such as polynucleotides, (i) so that their monomers pass through a signal generation region (or excitation zone, or the like) in sequence, and (ii) so that absorption dipoles of labels on monomer are oriented. That is, a nanopore constrains the movement of a polymer analyte, such as a polynucleotide, so that monomers, such as nucleotides, pass through a detection zone (or excitation region or like region) in single file, and so that labels on monomers are oriented or aligned so that they may be rendered selectively unresponsive to excitation by selection of a polarization state of an excitation beam. In some embodiments, additional features of nanopores include passing single stranded nucleic acids while not passing double stranded nucleic acids, or equivalently bulky molecules.

In some embodiments, nanopores used in connection with the methods and devices of the invention are provided in the form of arrays, such as an array of clusters of nanopores, which may be disposed regularly on a planar surface. In some embodiments, clusters are each in a separate resolution limited area so that optical signals from nanopores of different clusters are distinguishable by the optical detection system employed, but optical signals from nanopores within the same cluster cannot necessarily be assigned to a specific nanopore within such cluster by the optical detection system employed.

Solid state nanopores may be fabricated in a variety of materials including but not limited to, silicon nitride ($Si_3N_4$), silicon dioxide ($SiO_2$), and the like. The fabrication and operation of nanopores for analytical applications, such as DNA sequencing, are disclosed in the following exemplary references that are incorporated by reference: Ling, U.S. Pat. No. 7,678,562; Hu et al, U.S. Pat. No. 7,397,232; Golovchenko et al, U.S. Pat. No. 6,464,842; Chu et al, U.S. Pat. No. 5,798,042; Sauer et al, U.S. Pat. No. 7,001,792; Su et al, U.S. Pat. No. 7,744,816; Church et al, U.S. Pat. No. 5,795,782; Bayley et al, U.S. Pat. No. 6,426,231; Akeson et al, U.S. Pat. No. 7,189,503; Bayley et al, U.S. Pat. No. 6,916,665; Akeson et al, U.S. Pat. No. 6,267,872; Meller et al, U.S. patent publication 2009/0029477; Howorka et al, International patent publication WO2009/007743; Brown et al, International patent publication WO2011/067559; Meller et al, International patent publication WO2009/020682; Polonsky et al, International patent publication WO2008/092760; Van der Zaag et al, International patent publication WO2010/007537; Yan et al, Nano Letters, 5(6): 1129-1134 (2005); Iqbal et al, Nature Nanotechnology, 2: 243-248 (2007); Wanunu et al, Nano Letters, 7(6): 1580-1585 (2007); Dekker, Nature Nanotechnology, 2: 209-215 (2007); Storm et al, Nature Materials, 2: 537-540 (2003); Wu et al, Electrophoresis, 29(13): 2754-2759 (2008); Nakane et al, Electrophoresis, 23: 2592-2601 (2002); Zhe et al, J. Micromech. Microeng., 17: 304-313 (2007); Henriquez et al, The Analyst, 129: 478-482 (2004); Jagtiani et al, J. Micromech. Microeng., 16: 1530-1539 (2006); Nakane et al, J. Phys. Condens. Matter, 15 R1365-R1393 (2003); DeBlois et al, Rev. Sci. Instruments, 41(7): 909-916 (1970); Clarke et al, Nature Nanotechnology, 4(4): 265-270 (2009); Bayley et al, U.S. patent publication 2003/0215881; and the like.

In some embodiments, the invention comprises nanopore arrays with one or more light-blocking layers, that is, one or more opaque layers. Typically nanopore arrays are fabricated in thin sheets of material, such as, silicon, silicon nitride, silicon oxide, aluminum oxide, or the like, which readily transmit light, particularly at the thicknesses used, e.g. less than 50-100 nm. For electrical detection of analytes this is not a problem. However, in optically-based detection of labeled molecules translocating nanopores, light transmitted through an array invariably excites materials outside of intended reaction sites, thus generates optical noise, for example, from nonspecific background fluorescence, fluorescence from labels of molecules that have not yet entered a nanopore, or the like. In one aspect, the invention addresses this problem by providing nanopore arrays with one or more light-blocking layers that reflect and/or absorb light from an excitation beam, thereby reducing background noise for optical signals generated at intended reaction sites associated with nanopores of an array. In some embodiments, this permits optical labels in intended reaction sites to be excited by direct illumination. In some embodiments, an opaque layer may be a metal layer. Such metal layer may comprise Sn, Al, V, Ti, Ni, Mo, Ta, W, Au, Ag or Cu. In some embodiments such metal layer may comprise Al, Au, Ag or Cu. In still other embodiments, such metal layer may comprise aluminum or gold, or may comprise solely aluminum. The thickness of an opaque layer may vary widely and depends on the physical and chemical properties of material composing the layer. In some embodiments, the thickness of an opaque layer may be at least 5 nm, or at least 10 nm, or at least 40 nm. In other embodiments, the thickness of an opaque layer may be in the range of from 5-100 nm; in other embodiments, the thickness of an opaque layer may be in the range of from 10-80 nm. An opaque layer need not block (i.e. reflect or absorb) 100 percent of the light from an excitation beam. In some embodiments, an opaque layer may block at least 10 percent of incident light from an excitation beam; in other embodiments, an opaque layer may block at least 50 percent of incident light from an excitation beam.

Opaque layers or coatings may be fabricated on solid-state membranes by a variety of techniques known in the art. Material deposition techniques may be used including chemical vapor deposition, electrodeposition, epitaxy, thermal oxidation, physical vapor deposition, including evaporation and sputtering, casting, and the like. In some embodiments, atomic layer deposition may be used, e.g. U.S. Pat. No. 6,464,842; Wei et al, Small, 6(13): 1406-1414 (2010), which are incorporated by reference.

In some embodiments, a 1-100 nm channel or aperture may be formed through a solid substrate, usually a planar substrate, such as a membrane, through which an analyte, such as single stranded DNA, is induced to translocate. In other embodiments, a 2-50 nm channel or aperture is formed through a substrate; and in still other embodiments, a 2-30 nm, or a 2-20 nm, or a 3-30 nm, or a 3-20 nm, or a 3-10 nm channel or aperture if formed through a substrate. The solid-state approach of generating nanopores offers robustness and durability as well as the ability to tune the size and shape of the nanopore, the ability to fabricate high-density arrays of nanopores on a wafer scale, superior mechanical, chemical and thermal characteristics compared with lipid-based systems, and the possibility of integrating with electronic or optical readout techniques. Biological nanopores on the other hand provide reproducible narrow bores, or lumens, especially in the 1-10 nanometer range, as well as techniques for tailoring the physical and/or chemical properties of the nanopore and for directly or indirectly attaching groups or elements, such as fluorescent labels, which may be FRET donors or acceptors, by conventional protein engineering methods. Protein nanopores typically rely on delicate lipid bilayers for mechanical support, and the fabrication of solid-state nanopores with precise dimensions remains challenging. In some embodiments, solid-state nanopores may be combined with a biological nanopore to form a so-called "hybrid" nanopore that overcomes some of these shortcomings, thereby providing the precision of a biological pore protein with the stability of a solid state nanopore. For optical read out techniques a hybrid nanopore provides a precise location of the nanopore which simplifies the data acquisition greatly.

In some embodiments, clusters may also be formed by disposing protein nanopores in lipid bilayers supported by solid phase membrane containing an array of apertures. For example, such an array may comprise apertures fabricated (e.g. drilled, etched, or the like) in solid phase support. The geometry of such apertures may vary depending on the fabrication techniques employed. In some embodiments, each such aperture is associated with, or encompassed by, a separate resolution limited area; however, in other embodiments, multiple apertures may be within the same resolution limited area. The cross-sectional area of the apertures may vary widely and may or may not be the same as between different clusters, although such areas are usually substantially the same as a result of conventional fabrication approaches. In some embodiments, apertures have a minimal linear dimension (e.g. diameter in the case of circular apertures) in the range of from 10 to 200 nm, or have areas in the range of from about 100 to $3 \times 10^4$ $nm^2$. Across the apertures may be disposed a lipid bilayer. The distribution of protein nanopores per aperture may be varied, for example, by controlling the concentration of protein nanopores during inserting step. In such embodiments, clusters of nanopores may comprise a random number of nanopores. In some embodiments, in which protein nanopores insert randomly into apertures, clusters containing one or more apertures on average have a number of protein nanopores that is greater than zero; in other embodiments, such clusters have a number of protein nanopores that is greater than 0.25; in other embodiments, such clusters have a number of protein nanopores that is greater than 0.5; in other embodiments, such clusters have a number of protein nanopores that is greater than 0.75; in other embodiments, such clusters have a number of protein nanopores that is greater than 1.0.

In some embodiments, methods and devices of the invention comprise a solid phase membrane, such as a SiN membrane, having an array of apertures therethrough providing communication between a first chamber and a second chamber (also sometimes referred to as a "cis chamber" and a "trans chamber") and supporting a lipid bilayer on a surface facing the second, or trans, chamber. In some embodiments, diameters of the aperture in such a solid phase membrane may be in the range of 10 to 200 nm, or in the range of 20 to 100 nm. In some embodiments, such solid phase membranes further include protein nanopores inserted into the lipid bilayer in regions where such bilayer spans the apertures on the surface facing the trans chamber. In some embodiments, such protein nanopores are inserted from the cis side of the solid phase membrane using techniques described herein. In some embodiments, such protein nanopores have a structure identical to, or similar to, α-hemolysin in that it comprises a barrel, or bore, along an axis and at one end has a "cap" structure and at the other end has a "stem" structure (using the terminology from Song et al, Science, 274: 1859-1866 (1996)). In some embodiments using such protein nanopores, insertion into the lipid bilayer results in the protein nanopore being oriented so that its cap structure is exposed to the cis chamber and its stem structure is exposed to the trans chamber.

In some embodiments, the present invention may employ hybrid nanopores in clusters, particularly for optical-based nanopore sequencing of polynucleotides. Such nanopores comprise a solid-state orifice, or aperture, into which a protein biosensor, such as a protein nanopore, is stably inserted. A charged polymer may be attached to a protein nanopore (e.g. alpha hemolysin) by conventional protein engineering techniques after which an applied electric field may be used to guide a protein nanopore into an aperture in a solid-state membrane. In some embodiments, the aperture in the solid-state substrate is selected to be slightly smaller than the protein, thereby preventing it from translocating through the aperture. Instead, the protein will be embedded into the solid-state orifice.

Solid state, or synthetic, nanopores may be prepared in a variety of ways, as exemplified in the references cited above. In some embodiments a helium ion microscope may be used to drill the synthetic nanopores in a variety of materials, e.g. as disclosed by Yang et al, Nanotechnology, 22: 285310 (2011), which is incorporated herein by reference. A chip that supports one or more regions of a thin-film material, e.g. silicon nitride, that has been processed to be a free-standing membrane is introduced to the helium ion microscope (HIM) chamber. HIM motor controls are used to bring a free-standing membrane into the path of the ion beam while the microscope is set for low magnification. Beam parameters including focus and stigmation are adjusted at a region adjacent to the free-standing membrane, but on the solid substrate. Once the parameters have been properly fixed, the chip position is moved such that the free-standing membrane region is centered on the ion beam scan region and the beam is blanked. The HIM field of view is set to a dimension (in μm) that is sufficient to contain the entire anticipated nanopore pattern and sufficient to be useful in future optical readout (i.e. dependent on optical magnification, camera resolution, etc.). The ion beam is then rastered once through the entire field of view at a pixel dwell time that results in a total ion dose sufficient to remove all or most of the membrane autofluorescence. The field of view is then set to the proper value (smaller than that used above) to perform lithographically-defined milling of either a single nanopore or an array of nanopores. The pixel dwell time of the pattern is set to result in nanopores of one or more predetermined diameters, determined through the use of a calibration sample prior to sample processing. This entire process is repeated for each desired region on a single chip and/or for each chip introduced into the HIM chamber.

In some embodiments, a device for implementing the above methods for analyzing polymers (such as single stranded polynucleotides) typically includes a set of electrodes for establishing an electric field across the layered membrane and nanopores. Single stranded nucleic acids are exposed to nanopores by placing them in an electrolyte in a first chamber, which is configured as the "cis" side of the layered membrane by placement of a negative electrode in the chamber. Upon application of an electric field, the negatively single stranded nucleic acids are captured by nanopores and translocated to a second chamber on the other side of the layered membrane, which is configured as the "trans" side of membrane by placement of a positive electrode in the chamber. The speed of translocation depends in part on the ionic strength of the electrolytes in the first and second chambers and the applied voltage across the nanopores. In optically based detection, a translocation speed may be selected by preliminary calibration measurements, for example, using predetermined standards of labeled single stranded nucleic acids that generate signals at different expected rates per nanopore for different voltages. Thus, for DNA sequencing applications, a translocation speed may be selected based on the signal rates from such calibration measurements. Consequently, from such measurements a voltage may be selected that permits, or maximizes, reliable nucleotide identifications, for example, over an array of nanopores. In some embodiments, such calibrations may be made using nucleic acids from the sample of templates being analyzed (instead of, or in addition to, predetermined standard sequences). In some embodiments, such calibrations may be carried out in real time during a sequencing run and the applied voltage may be modified in real time based on such measurements, for example, to maximize the acquisition of nucleotide-specific signals.

Controlling translocation speeds of polymers through nanopores is necessary to permit collection of data from which sequence information can be obtained. Translocation speeds depend in part on the voltage difference (or electrical field strength) across a nanopore and conditions in the reaction mixture of the first chamber where nucleic acid polymers are exposed to the nanopores (e.g. disposed in a solid phase membrane making up one wall of the first chamber). Nucleic acid polymer capture rates by nanopores depend on concentration of such polymers. In some embodiments, conventional reaction mixture conditions for nanopore sequencing may be employed with the invention, for example, 1M KCl (or equivalent salt, such as NaCl, LiCl, or the like) and a pH buffering system (which, for example, ensures that proteins being used, e.g. protein nanopores, nucleases, or the like, are not denatured). In some embodiments, a pH buffering system may be used to keep the pH substantially constant at a value in the range of 6.8 to 8.8. In some embodiments, a voltage difference across the nanopores may be in the range of from 70 to 200 mV. In other embodiments, a voltage difference across the nanopores may be in the range of from 80 to 150 mV. An appropriate voltage for operation may be selected using conventional measurement techniques. Current (or voltage) across a nanopore may readily be measured using commercially available instruments. A voltage difference may be selected so that translocation speed is within a desired range. In some embodiments, a range of translocation speeds comprises those speeds less than 1000 nucleotides per second. In other embodiments, a range of translocation speeds is from 10 to 800 nucleotides per second; in other embodiments, a range of translocation speeds is from 10 to 600 nucleotides per second; in other embodiments, a range of translocation speeds is from 200 to 800 nucleotides per second; in other embodiments, a range of translocation speeds is from 200 to 500 nucleotides per second.

Embodiments Employing Two or Three Optical Labels

In some embodiments, as few as two different kinds of nucleotide are labeled with different optical labels that generate distinguishable optical signals for the selected kinds of nucleotide in both sense strands and antisense strands of target polynucleotides. For example, C's and T's of the complementary strands of each target polynucleotide may be replaced by labeled analogs, wherein the labels of the C and T analogs are capable of generating distinct optical signals. Optical signatures are then generated by translocating the labeled strands through nanopores where nucleotides of the strands are constrained to pass sequentially through an optical detection region where their labels are caused to generate optical signals. In some embodiments, information from optical signatures from both sense and antisense strands are combined to determine a nucleotide sequence of target polynucleotides.

In some embodiments, the selected kinds of nucleotides of target polynucleotides are replaced by labeled nucleotide analogs in an extension reaction using a nucleic acid polymerase. Labeled strands of target polynucleotides are translocated through nanopores that constrain the nucleotides of strands to move single file through an optical detection region where they are excited so that they produce an optical signal. A collection of optical signals for an individual strand is referred to herein as an optical signature of the strand. In some embodiments, where a strand and its complement (i.e. sense and antisense strands) are linked, for example, via a hairpin adaptor, a single optical signature may include optical signals from optical labels on nucleotides from both the sense strand and the antisense strand. In other embodiments, different strands of a target polynucleotide may separately generate two different optical signatures which may be combined, or used together, for analysis, as mentioned above. Such separately analyzed strands may be associated after generation of optical signatures, for example, by using molecular tags (which may be, for example, oligonucleotide segments attached to target polynucleotides in a known position, length and sequence pattern and diversity to permit ready association). As noted below, optical signature of the invention may comprise mixed optical signals in that the signal detected in each detection interval may comprise contributions from multiple optical labels emitting within a resolution limited area or volume; that is, they may (for example) be mixed FRET signals, as described by Huber et al, U.S. patent publication US20160076091, which is incorporated herein by reference.

As mentioned above, in some embodiments, methods of the invention may be implemented with the following steps: (a) copying a strand of a double stranded polynucleotide so that nucleotide analogs with distinct optical labels are substituted for at least two kinds of nucleotide to form a labeled strand; (b) copying a complement of the strand so that said nucleotide analogs are substituted for the same at least two kinds of nucleotide to form a labeled complement; (c) translocating the labeled stand through a nanopore so that the nucleotides of the labeled strand pass single file through an excitation zone where optical labels are excited to generate optical signals; (d) detecting a time series of optical signals from the optical labels as the labeled strand translocates through the nanopore to produce a strand optical signature; (e) translocating the labeled complement through a nanopore so that the nucleotides of the labeled complement pass single file through an excitation zone where optical labels are excited to generate optical signals; (f) detecting a time series of optical signals from the optical labels as the labeled complement translocates through the nanopore to produce a complement optical signature; (g) determining a sequence of the double stranded polynucleotide from the strand optical signature and the complement optical signature. In some embodiments, two kinds of nucleotide are labeled, which may be C's and T's, C's and G's, C's and A's, T's and G's, T's and A's, or G's and A's. In some embodiments, pyrimidine nucleotides are labeled. In other embodiments, purine nucleotides are labeled. In some embodiments, selected kinds of nucleotides of a strand are labeled by incorporating labeled analog dNTPs of the selected kind of nucleotides in a primer extension reaction using a nucleic acid polymerase. In other embodiments, selected kinds of nucleotides of a strand are labeled by incorporating analog dNTPs of the selected kinds of nucleotides in an extension reaction, wherein the analog dNTPs are derivatized with orthogonally reactive functionalities that allow attachment of different labels to different kinds of nucleotides in a subsequent reaction. This latter labeling approach is disclosed in Jett et al, U.S. Pat. No. 5,405,747, which is incorporated herein by reference.

In some embodiments, three kinds of nucleotide are labeled, which may include labeling C's with a first optical label, T's with a second optical label, and G's and A's with a third optical label. In other embodiments, the following groups of nucleotides may be labeled as indicated: C's and G's with a first optical label and second optical label, respectively, and T's and A's with a third optical label; C's and A's with a first optical label and second optical label, respectively, and T's and G's with a third optical label; T's and G's with a first optical label and second optical label, respectively, and C's and A's with a third optical label; A's and G's with a first optical label and second optical label, respectively, and T's and C's with a third optical label.

In some embodiments, optical labels are fluorescent acceptor molecules that generate a fluorescent resonance energy transfer (FRET) signal after energy transfer from a donor associated with a nanopore. In some embodiments, as described further below, donors may be optically active nanoparticles, such as, quantum dots, nanodiamonds, or the like. Selection of particular combinations of acceptor molecules and donors are design choices for one of ordinary skill in the art. In some embodiments, some of which are described more fully below, a single quantum dot is attached to a nanopore and is excited to fluoresce using an excitation beam whose wavelength is sufficiently separated, usually lower (i.e. bluer), so that it does not contribute to FRET signals generated by acceptors. Likewise, a quantum dot is selected whose emission wavelength overlaps the absorption bands of both acceptor molecules to facilitate FRET interactions. In some embodiments, two donors may be used for each excitation zone of a nanopore, wherein the emission wavelength of each is selected to optimally overlap the absorption band of a different one of the acceptor molecules.

Figure 7A:
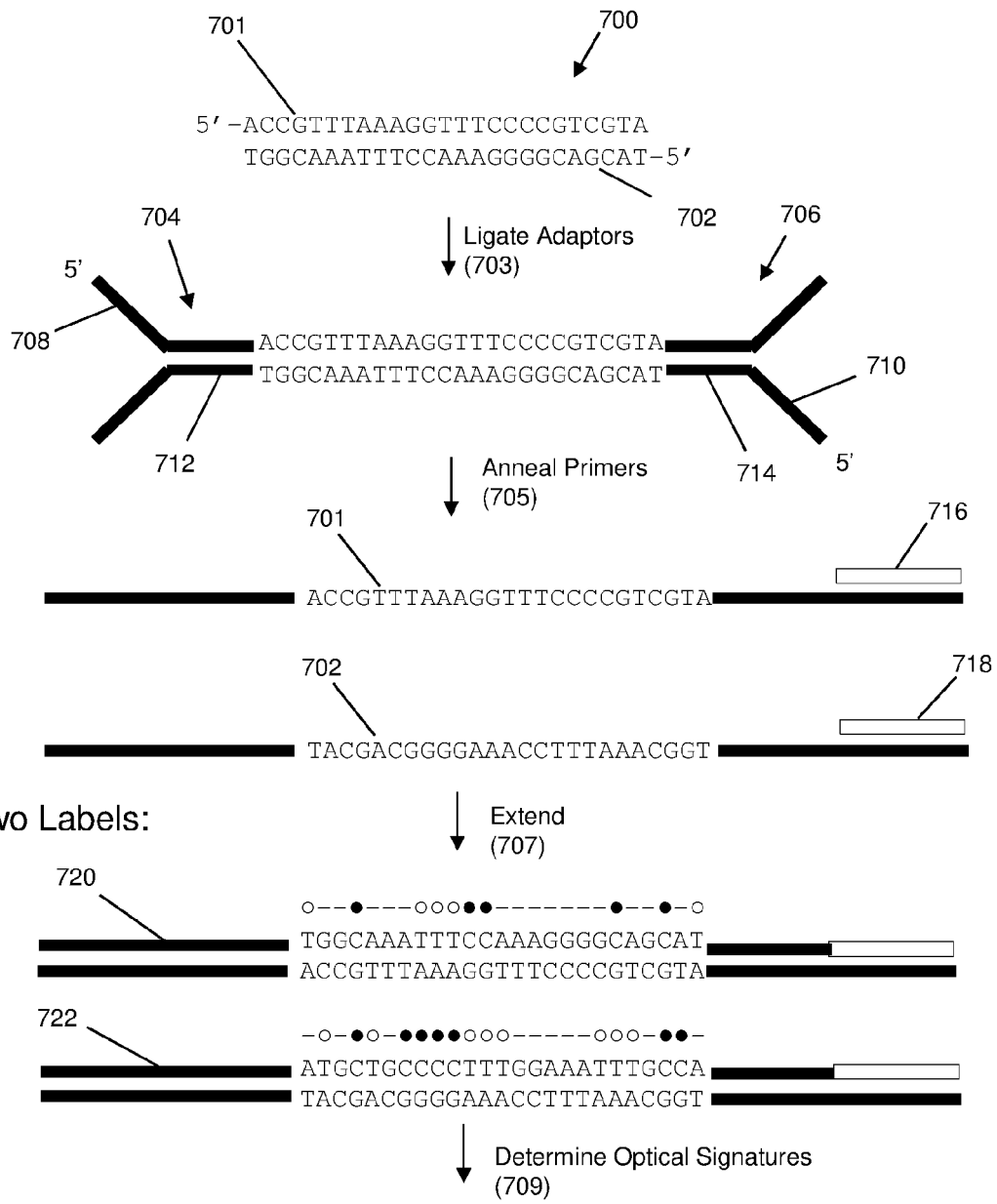

In FIG. 7A, double stranded target polynucleotide (700) consists of sense strand (701) (SEQ ID NO. 1) and complementary antisense strand (702) (SEQ ID NO. 2), to which is ligated (703) "Y" adaptors (704) and (706) using conventional methods, e.g. Weissman et al, U.S. Pat. No. 6,287,825; Schmitt et al, U.S. patent publication US2015/004468; which are incorporated herein by reference. Arms (708) and (710) of adaptors (704 and 706, respectively) include primer binding sites to which primers (716) and (718) are annealed (705). Double stranded portions (712) and (714) may include tag sequences, e.g. one or both may include randomers of predetermined length and composition, which may be used for later re-association of the strands, for example, to obtain sequence information from the respective optical signatures of the strands. After annealing primers (716) and (718), they may be extended (707) by a nucleic acid polymerase in the presence of (for example, as illustrated) labeled dUTP analogs (labels shown as open circles in the incorporated nucleotides) and labeled dCTP analogs (labels shown as filled circles in the incorporated nucleotides) and natural unlabeled dGTPs and dATPs (with neither unlabeled dTTP nor unlabeled dCTP being present so that the analogs are fully substituted in the extended strands). The absence of labels on G's and A's are illustrated as dashes above the incorporated nucleotides. In an ideal detection system without noise, the sequence of open circles, filled circles and dashes would be good representations of optical signatures generated by the indicated sense and antisense strands as they pass through an excitation zone of a nanopore.

In FIG. 7B, extension products (720) and (722) are illustrated for an alternative embodiment employing three labels. Incorporated labeled dUTP analogs are shown as open circles and incorporated labeled dCTP analogs are shown as filled circles, as above. Incorporated labeled dATP and dGTP analogs are shown as filled diamonds.

Guidance in selecting the kinds of nucleotide to label, kinds of labels and linkers for attaching them to bases, and nucleic acid polymerases for extension reactions in the presence of dNTP analogs can be found in the following references, which are incorporated by reference: Goodman et al, U.S. Pat. No. 5,945,312; Jett et al, U.S. Pat. No. 5,405,747; Muehlegger et al, U.S. patent publication US2004/0214221; Giller et al, Nucleic Acids Research, 31(10): 2630-2635 (2003); Tasara et al, Nucleic Acids Research, 31(10): 2636-2646 (2003); Augustin et al, J. Biotechnology, 86: 289-301 (2001); Brakmann, Current Pharmaceutical Biotechnology, 5(1): 119-126 (2004); and the like. Exemplary nucleic acid polymerases for use with the invention include, but are not limited to, Vent exo−, Taq, E. coli Pol I, Tgo exo−, Klenow fragment exo−, Deep Vent exo−, and the like. In some embodiments, exemplary nucleic acid polymerases include, but are not limited to, Vent exo and Klenow fragment exo−. Exemplary fluorescent labels for dNTP analogs include, but are not limited to, ALEXA 488, AMCA, Atto 655, Cy3, Cy5, Evoblue 30, fluorescein, Gnothis blue 1, Gnothis blue 2, Gnothis blue 3, Dy630, Dy635, MR121, rhodamine, Rhodamine Green, OREGON GREEN, TAMRA, and the like. Exemplary fluorescent labels for dUTP analogs include, but are not limited to, ALEXA 488, AMCA, Atto 655, Cy3, Cy5, Dy630, Dy665, Evoblue 30, Evoblue 90, fluorescein, Gnothis blue 1, Gnothis blue 2, Gnothis blue 3, MR121, OREGON GREEN, rhodamine, Rhodamine Green, TAMRA, and the like. Exemplary fluorescent labels for dCTP analogs include, but are not limited to, Atto 655, Cy5, Evoblue 30, Gnothis blue 3, rhodamine, Rhodamine Green, TAMRA, and the like. Exemplary fluorescent labels for dATP analogs include, but are not limited to, Atto 655, Cy5, Evoblue 30, Gnothis blue 3, Rhodamine Green, and the like. Exemplary fluorescent labels for dGTP analogs include, but are not limited to, Evoblue 30, Gnothis blue 3, Rhodamine Green, and the like. Exemplary pairs of fluorescent labels for dUTP analogs and dCTP analogs include, but are not limited to, (TAMRA, Rhodamine Green), (Atto 655, Evoblue 30), (Evoblue 30, Atto 655), (Evoblue 30, Gnothis blue 3), (Evoblue 30, Rhodamine Green), (Gnothis blue 1, Rhodamine Green), (Gnothis blue 2, Atto 655), Gnothis blue 3, Cy5), and the like.

Figure 7C:
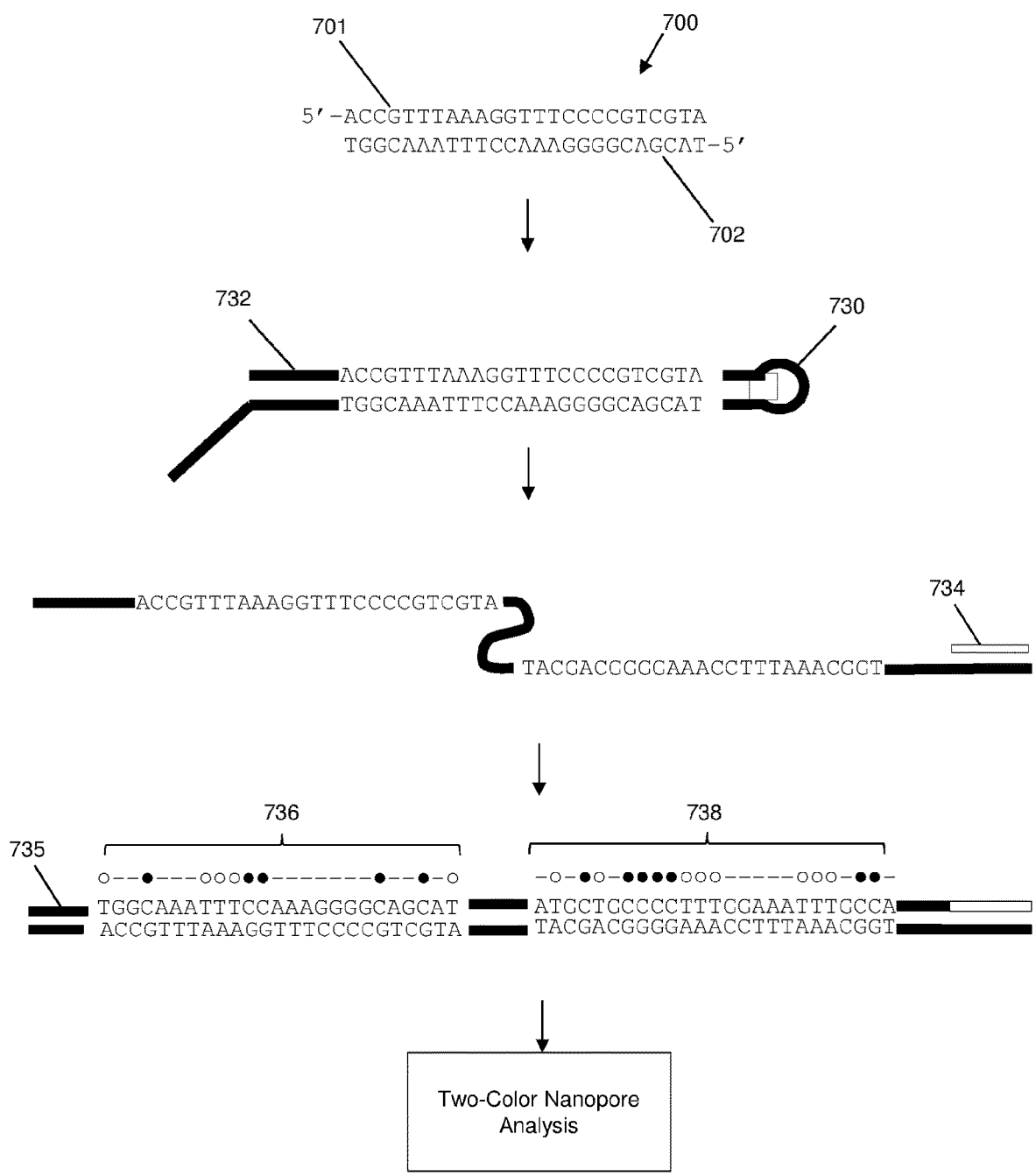

FIG. 7C illustrates an embodiment in which two labels are used and sense and antisense strands are linked by means of hairpin adaptor (730), for example, as taught in U.S. patent publications US 2015/0152492 and US 2012/0058468, which are incorporated herein by reference. Tailed adaptor (732) and hairpin adaptor (730) are ligated to target polynucleotide (700). After denaturation and annealing of primer (734), an extension reaction produces extension product (735) which includes segment (736), the labeled complement of strand (701) (SEQ ID NO. 1) and segment (738), the labeled reverse complement of strand (701) (SEQ ID NO. 1). After translocation of extension product (735) through a nanopore and generation of an optical signature the sequence of target polynucleotide (700) can be determined. Optionally, the sequence of hairpin (730) may be selected so that a predetermined pattern of labels is incorporated during the extension reaction, which may be used to assist in the analysis of the optical signature, e.g. by indicating where segment (736) ends and where segment (738) begins, or the like.

Definitions

"Evanescent field" means a non-propagating electromagnetic field; that is, it is an electromagnetic field in which the average value of the Poynting vector is zero.

"FRET" or "Förster, or fluorescence, resonant energy transfer" means a non-radiative dipole-dipole energy transfer mechanism from an excited donor fluorophore to an acceptor fluorophore in a ground state. The rate of energy transfer in a FRET interaction depends on the extent of spectral overlap of the emission spectrum of the donor with the absorption spectrum of the acceptor, the quantum yield of the donor, the relative orientation of the donor and acceptor transition dipoles, and the distance between the donor and acceptor molecules, Lakowicz, Principles of Fluorescence Spectroscopy, Third Edition (Springer, 2006). FRET interactions of particular interest are those which result a portion of the energy being transferred to an acceptor, in turn, being emitted by the acceptor as a photon, with a frequency lower than that of the light exciting its donor (i.e. a "FRET signal"). "FRET distance" means a distance between a FRET donor and a FRET acceptor over which a FRET interaction can take place and a detectable FRET signal produced by the FRET acceptor.

"Kit" refers to any delivery system for delivering materials or reagents for carrying out a method of the invention. In the context of reaction assays, such delivery systems include systems that allow for the storage, transport, or delivery of reaction reagents (e.g., fluorescent labels, such as mutually quenching fluorescent labels, fluorescent label linking agents, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second or more containers contain mutually quenching fluorescent labels.

"Nanopore" means any opening positioned in a substrate that allows the passage of analytes through the substrate in a predetermined or discernable order, or in the case of polymer analytes, passage of their monomeric units through the substrate in a predetermined or discernible order. In the latter case, a predetermined or discernible order may be the primary sequence of monomeric units in the polymer. Examples of nanopores include proteinaceous or protein based nanopores, synthetic or solid state nanopores, and hybrid nanopores comprising a solid state nanopore having a protein nanopore embedded therein. A nanopore may have an inner diameter of 1-10 nm or 1-5 nm or 1-3 nm. Examples of protein nanopores include but are not limited to, alpha-hemolysin, voltage-dependent mitochondrial porin (VDAC), OmpF, OmpC, MspA and LamB (maltoporin), e.g. disclosed in Rhee, M. et al., Trends in Biotechnology, 25(4) (2007): 174-181; Bayley et al (cited above); Gundlach et al, U.S. patent publication 2012/0055792; and the like, which are incorporated herein by reference. Any protein pore that allows the translocation of single nucleic acid molecules may be employed. A nanopore protein may be labeled at a specific site on the exterior of the pore, or at a specific site on the exterior of one or more monomer units making up the pore forming protein. Pore proteins are chosen from a group of proteins such as, but not limited to, alpha-hemolysin, MspA, voltage-dependent mitochondrial porin (VDAC), Anthrax porin, OmpF, OmpC and LamB (maltoporin). Integration of the pore protein into the solid state hole is accomplished by attaching a charged polymer to the pore protein. After applying an electric field the charged complex is electrophoretically pulled into the solid state hole. A synthetic nanopore, or solid-state nanopore, may be created in various forms of solid substrates, examples of which include but are not limited to silicones (e.g. Si3N4, SiO2), metals, metal oxides (e.g. Al2O3) plastics, glass, semiconductor material, and combinations thereof. A synthetic nanopore may be more stable than a biological protein pore positioned in a lipid bilayer membrane. A synthetic nanopore may also be created by using a carbon nanotube embedded in a suitable substrate such as but not limited to polymerized epoxy. Carbon nanotubes can have uniform and well-defined chemical and structural properties. Various sized carbon nanotubes can be obtained, ranging from one to hundreds of nanometers. The surface charge of a carbon nanotube is known to be about zero, and as a result, electrophoretic transport of a nucleic acid through the nanopore becomes simple and predictable (Ito, T. et al., Chem. Commun. 12 (2003): 1482-83). The substrate surface of a synthetic nanopore may be chemically modified to allow for covalent attachment of the protein pore or to render the surface properties suitable for optical nanopore sequencing. Such surface modifications can be covalent or non-covalent. Most covalent modification include an organosilane deposition for which the most common protocols are described: 1) Deposition from aqueous alcohol. This is the most facile method for preparing silylated surfaces. A 95% ethanol-5% water solution is adjusted to pH 4.5-5.5 with acetic acid. Silane is added with stirring to yield a 2% final concentration. After hydrolysis and silanol group formation the substrate is added for 2-5 min. After rinsed free of excess materials by dipping briefly in ethanol. Cure of the silane layer is for 5-10 min at 110 degrees Celsius. 2) Vapor Phase Deposition. Silanes can be applied to substrates under dry aprotic conditions by chemical vapor deposition methods. These methods favor monolayer deposition. In closed chamber designs, substrates are heated to sufficient temperature to achieve 5 mm vapor pressure. Alternatively, vacuum can be applied until silane evaporation is observed. 3) Spin-on deposition. Spin-on applications can be made under hydrolytic conditions which favor maximum functionalization and polylayer deposition or dry conditions which favor monolayer deposition. In some embodiments, single nanopores are employed with methods of the invention. In other embodiments, a plurality of nanopores are employed. In some of the latter embodiments, a plurality of nanopores is employed as an array of nanopores, usually disposed in a planar substrate, such as a solid phase membrane. Nanopores of a nanopore array may be spaced regularly, for example, in a rectilinear pattern, or may be spaced randomly. In a preferred embodiment, nanopores are spaced regularly in a rectilinear pattern in a planar solid phase substrate.

"Nanostructure" (used interchangeably with "nanoscale structure" and "nanoscale feature") means a structure that has at least one dimension within a range of a few nanometers to several hundred nanometers, for example, from 1 to 1000 nanometers. In some applications, such range is from 2 to 500 nanometers; in other applications, such range is from 3 to 500 nanometers. The shape and geometry of nanostructures may vary widely and include, but are not limited to, nanopores, nanowells, nanoparticles, and any other convenient shapes particularly suitable for carrying out sequences of reactions. In some embodiments, nanostructures may be protein nanopores operationally associated with a solid phase membrane. Some nanostructures, such as, nanopores and nanowells, may be formed in a larger common substrate, such as a solid phase membrane, or other solid, to form arrays of nanopores or nanowells. Nanostructures of particular interest are those capable of supporting or containing a chemical, physical (e.g. FRET), enzymatic and/or binding reaction or a sequence of such reactions. In some embodiments, a nanostructure, such as a nanowell, encloses a volume that is less than one nanoliter (10×−9 liter), less than one picoliter, or less than one femtoliter. In other embodiments, each of the individual nanowells provides a volume that is less than 1000 zeptoliters, 100 zeptoliters, 80 zeptoliters, or less than 50 zeptoliters, or less than 1 zeptoliter, or even less than 100 yactoliters. In some embodiments, nanowells comprise zero mode waveguides.

"Polymer" means a plurality of monomers connected into a linear chain. Usually, polymers comprise more than one type of monomer, for example, as a polynucleotide comprising A's, C's, G's and T's, or a polypeptide comprising more than one kind of amino acid. Monomers may include without limitation nucleosides and derivatives or analogs thereof and amino acids and derivatives and analogs thereof.

In some embodiments, polymers are polynucleotides, whereby nucleoside monomers are connected by phosphodiester linkages, or analogs thereof.

"Polynucleotide" or "oligonucleotide" are used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references. Likewise, the oligonucleotide and polynucleotide may refer to either a single stranded form or a double stranded form (i.e. duplexes of an oligonucleotide or polynucleotide and its respective complement). It will be clear to one of ordinary skill which form or whether both forms are intended from the context of the terms usage.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide.

Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, 2nd Edition (Cold Spring Harbor Press, New York, 2003).

"Resolution limited area" is an area of a surface of a nanopore or nanowell array within which individual features or light emission sources cannot be distinguished by an optical signal detection system. Without intending to be limited by theory, such resolution limited area is determined by a resolution limit (also sometimes referred to as a "diffraction limit" or "diffraction barrier") of an optical system. Such limit is determined by the wavelength of the emission source and the optical components and may be defined by $d=\lambda/NA$, where d is the smallest feature that can be resolved, $\lambda$ is the wavelength of the light and NA is the numerical aperture of the objective lens used to focus the light. Thus, whenever two or more nanopores are within a resolution limited area and two or more optical signals are generated at the respective nanopores, an optical detection system cannot distinguish or determine which optical signals came from which nanopore. In accordance with the invention, a surface of a nanopore array may be partitioned, or subdivided, into non-overlapping regions, or substantially non-overlapping regions, corresponding to resolution limited areas. The size of such subdivisions corresponding to resolution limited areas may depend on a particular optical detection system employed. In some embodiments, whenever light emission sources are within the visible spectrum, a resolution limited area is in the range of from 300 nm$^2$ to 3.0 µm$^2$; in other embodiments, a resolution limited area is in the range of from 1200 nm$^2$ to 0.7 µm$^2$; in other embodiments, a resolution limited area is in the range of from $3\times10^4$ nm$^2$ to 0.7 µm$^2$, wherein the foregoing ranges of areas are in reference to a surface of a nanopore or nanowell array. In some embodiments, the visible spectrum means wavelengths in the range of from about 380 nm to about 700 nm.

"Sequence determination", "sequencing" or "determining a nucleotide sequence" or like terms in reference to polynucleotides includes determination of partial as well as full sequence information of the polynucleotide. That is, the terms include sequences of subsets of the full set of four natural nucleotides, A, C, G and T, such as, for example, a sequence of just A's and C's of a target polynucleotide. That is, the terms include the determination of the identities, ordering, and locations of one, two, three or all of the four types of nucleotides within a target polynucleotide. In some embodiments, the terms include the determination of the identities, ordering, and locations of two, three or all of the four types of nucleotides within a target polynucleotide. In some embodiments sequence determination may be accomplished by identifying the ordering and locations of a single type of nucleotide, e.g. cytosines, within the target polynucleotide "catcgc . . . " so that its sequence is represented as a binary code, e.g. "100101 . . . " representing "c-(not c)(not c)c-(not c)-c . . . " and the like. In some embodiments, the terms may also include subsequences of a target polynucleotide that serve as a fingerprint for the target polynucleotide; that is, subsequences that uniquely identify a target polynucleotide, or a class of target polynucleotides, within a set of polynucleotides, e.g. all different RNA sequences expressed by a cell.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

What is claimed is:

1. A method of analyzing a polynucleotide comprising:
   directing to a nanopore an excitation beam having a predetermined polarization state;
   translocating a polynucleotide through the nanopore, wherein nucleotides of the polynucleotide are labeled with fluorescent labels having absorption dipoles and wherein the nanopore spatially orients the fluorescent labels so that during translocation the absorption dipoles are substantially unresponsive to the excitation beam;

detecting changes in fluorescent signals generated by the fluorescent labels as nucleotides with fluorescent labels exit the nanopore and absorption dipoles thereof become responsive to excitation by the excitation beam with the predetermined polarization state; and identifying nucleotides exiting the nanopore from the changes in fluorescent signals.

2. The method of claim 1 wherein the polynucleotide comprises different kinds of nucleotides that are labeled with fluorescent labels that emit distinct fluorescent signals for the different kinds of labeled nucleotides.

3. The method of claim 1 wherein said fluorescent labels are mutually quenching.

4. The method of claim 1 wherein said translocating includes translocating in the presence of one or more quenching agents.

5. The method of claim 1 wherein said nanopore comprises a protein nanopore.

6. The method of claim 1 wherein said predetermined polarization state has an electrical field vector and wherein said absorption dipoles of said fluorescent labels in said nanopore are substantially orthogonal to the electrical field vector of said predetermined polarization state.

7. A method of analyzing a polynucleotide comprising:
directing to a nanopore an excitation beam comprising a predetermined polarization state;

translocating a polynucleotide through the nanopore, wherein nucleotides of the polynucleotide are labeled with fluorescent labels having absorption dipoles and wherein the nanopore spatially orients the fluorescent labels so that during translocation absorption dipoles are maximally responsive to excitation by the excitation beam in the predetermined polarization state;

detecting optical signals generated by the fluorescent labels on nucleotides within the nanopore; and identifying nucleotides of the polynucleotide from the optical signals.

8. The method of claim 7 wherein the polynucleotide comprises different kinds of nucleotides that are labeled with fluorescent labels that emit distinct fluorescent signals for the different kinds of labeled nucleotides.

9. The method of claim 8 wherein said fluorescent labels are mutually quenching.

10. The method of claim 8 wherein said translocating includes translocating in the presence of one or more quenching agents.

11. The method of claim 7 wherein said nanopore comprises a protein nanopore.

12. The method of claim 7 wherein said predetermined polarization state has an electrical field vector and wherein said absorption dipoles of said fluorescent labels in said nanopore are substantially aligned with the electrical field vector of said predetermined polarization state.

13. A method of analyzing a polynucleotide comprising:
directing to a nanopore an excitation beam comprising a predetermined polarization state;

translocating a polynucleotide through a nanopore, wherein different kinds of nucleotide of the polynucleotide are labeled with different fluorescent labels, each having an absorption dipole and emitting a distinguishable optical signal, and wherein the nanopore spatially orients the fluorescent labels so that during translocation absorption dipoles are maximally responsive to excitation by the excitation beam in the predetermined polarization state;

detecting from pluralities of nucleotides within the nanopore a time-ordered set of optical signals as the polynucleotide passes through the nanopore;

separating optical signals from the different kinds of nucleotide to form nucleotide-specific time-ordered sets of optical signals; and determining a sequence of nucleotides from the nucleotide-specific time-ordered sets of optical signals.

14. The method of claim 13 wherein said determining includes forming candidate sequences from overlapping segments of nucleotides determined from said nucleotide-specific time-ordered sets of optical signals.

15. The method of claim 14 wherein the polynucleotide comprises different kinds of nucleotides that are labeled with fluorescent labels that emit distinct fluorescent signals for the different kinds of labeled nucleotides.

16. The method of claim 15 wherein said fluorescent labels are mutually quenching.

17. The method of claim 15 wherein said translocating includes translocating in the presence of one or more quenching agents.

18. The method of claim 13 wherein said nanopore comprises a protein nanopore.

19. The method of claim 13 wherein said predetermined polarization state has an electrical field vector and wherein said absorption dipoles of said fluorescent labels in said nanopore are substantially aligned with the electrical field vector of said predetermined polarization state.

* * * * *